(12) United States Patent
Menn et al.

(10) Patent No.: US 7,419,495 B2
(45) Date of Patent: Sep. 2, 2008

(54) TRIGGER LOCKOUT DEVICE FOR CLIP APPLYING INSTRUMENT

(75) Inventors: Pavel Menn, Marblehead, MA (US); Emmanuel Manetakis, Burlington, MA (US); Peter Aliski, Malden, MA (US)

(73) Assignee: Microline Pentax Inc., Beverly, MA (US)

(*) Notice: Subject to any disclaimer, the term of this patent is extended or adjusted under 35 U.S.C. 154(b) by 9 days.

(21) Appl. No.: 11/210,832

(22) Filed: Aug. 25, 2005

(65) Prior Publication Data

US 2007/0049948 A1 Mar. 1, 2007

(51) Int. Cl.
*A61B 17/10* (2006.01)
*A61B 17/04* (2006.01)
*B31B 1/00* (2006.01)

(52) U.S. Cl. .................. 606/143; 227/175.4; 227/19
(58) Field of Classification Search ... 227/175.1–175.4; 606/139, 142
See application file for complete search history.

(56) References Cited

U.S. PATENT DOCUMENTS

| | | | |
|---|---|---|---|
| 5,282,808 A | | 2/1994 | Kovac et al. |
| 5,527,320 A | * | 6/1996 | Carruthers et al. ........... 606/143 |
| 5,706,997 A | * | 1/1998 | Green et al. ............. 227/175.2 |
| 5,810,845 A | | 9/1998 | Yoon |
| 6,155,473 A | * | 12/2000 | Tompkins et al. ........ 227/175.2 |
| 6,258,107 B1 | * | 7/2001 | Balazs et al. ................. 606/153 |
| 6,277,131 B1 | * | 8/2001 | Kalikow ..................... 606/143 |
| 6,773,438 B1 | | 8/2004 | Knodel et al. |
| 7,059,508 B2 | * | 6/2006 | Shelton et al. ........... 227/175.2 |
| 2003/0040759 A1 | * | 2/2003 | de Guillebon et al. ....... 606/142 |
| 2003/0135224 A1 | | 7/2003 | Blake, III |

FOREIGN PATENT DOCUMENTS

EP 1199038 4/2002

OTHER PUBLICATIONS

U.S. Appl. No. 11/210,828 to Theroux et al., filed Aug. 25, 2005.
U.S. Appl. No. 11/210,830 to Menn et al., filed Aug. 25, 2005.
U.S. Appl. No. 11/210,836 to Manetakis, filed Aug. 25, 2005.
U.S. Appl. No. 11/210,837 to Theroux et al., filed Aug. 25, 2005.
U.S. Appl. No. 11/210,885 to Menn et al., filed Aug. 25, 2005.

* cited by examiner

*Primary Examiner*—Todd E. Manahan
*Assistant Examiner*—Christina D Gettman
(74) *Attorney, Agent, or Firm*—Greenblum & Bernstein, P.L.C.

(57) ABSTRACT

A trigger lockout device for a clip applying instrument. The lockout device includes a displaceable slider actuable by squeezing a trigger slidable in first and second directions a longitudinal axial direction within the barrel, and a block disposed within the barrel. When a first number of clips have not been applied and when the trigger is squeezed, the slider slidably engages and displaces the block and slides along a path in the axial direction to retrieve a clip of the first number of clips, and to insert the clip into the pair of jaws, and when a second number or none of the clips have not been applied, the slider engages the block to substantially prevent the slider from sliding along the path in at least one of the first or second directions such that the triggery cannot be unsqueezed.

20 Claims, 45 Drawing Sheets

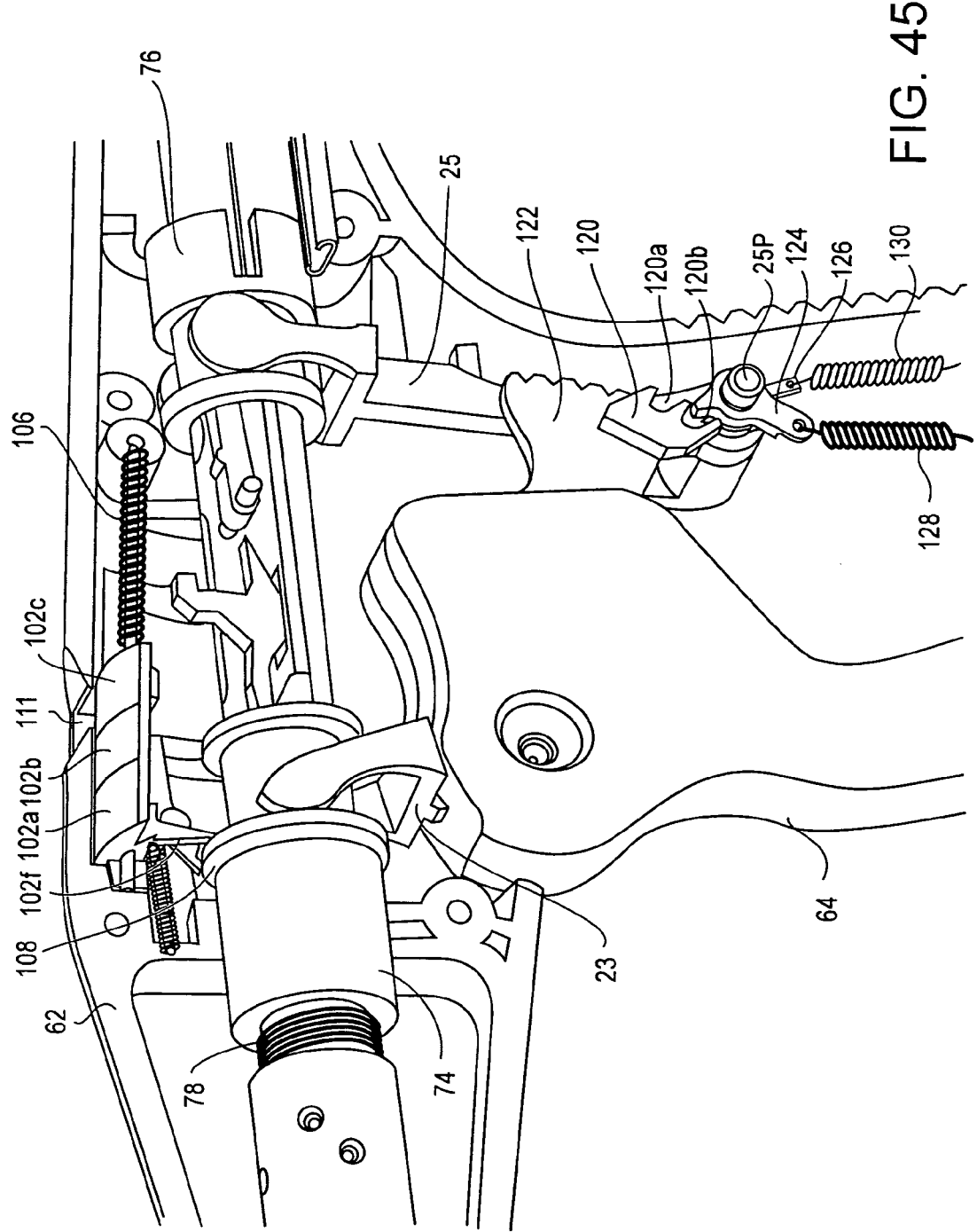

TRIGGER LOCKOUT DEVICE FOR CLIP APPLYING INSTRUMENT

BACKGROUND OF THE INVENTION

1. Field of the Invention

The present invention is related to a trigger lockout device, and more particularly relates to a trigger lockout device for a clip applying instrument.

2. Background and Material Information

Laparoscopic surgery is generally defined as minimally invasive surgery upon a patient, utilizing small or miniaturized medical devices by which body tissue is cut, removed or cauterized by small manipulable tools/devices through small incisions or openings within the patient's body. One such tool is a clip applier, which is used to grasp and/or crimp/seal tissue by the single hand of an operating surgeon, and is described in commonly-assigned U.S. Patent Publication No. 2003/0040759 and U.S. Pat. No. 6,277,131, the entire contents of both documents being expressly incorporated by reference herein.

Prior art clip appliers have a patient-engaging distalmost end with a pair of squeezable jaws arranged on the distal end of an elongated channel or frame. The elongated channel is surrounded by an elongated tube, which elongated tube and elongated channel are secured at their respective proximalmost ends to the distal end of a pistol-like handle grip assembly. The handle grip assembly includes an arcuately movable squeezable trigger. By squeezing the trigger towards a housing portion of the handle grip assembly, a clip is advanced through the elongated channel and into the jaws from an elongated ladder-like clip supply cartridge disposed through the elongated housing. The actuating sequence includes the squeezing of the trigger to close the jaws and thus crimp the clip between the jaws, then releasing the trigger to advance a new clip into location between the jaws awaiting the next squeezing of the trigger. The elongated clip supply cartridge is fed into a receiving slot or port in the proximal end of the handle grip assembly. Once all of the clips have been discharged from the cartridge, the cartridge may be removed from the clip applier and discarded, and the clip applier may be sterilized and reused.

It is also noted that once all of the clips have been discharged from the applier, there exists the danger that the surgeon may attempt to apply a clip anyway (not realizing that all the clips have been discharged), thereby letting the jaws close upon the tissue (without applying a clip) and potentially damaging the tissue and increasing the duration of the medical procedure and the risk of complications. Therefore, a need has arisen to prevent the surgeon from attempting to apply a clip when there are no more clips left in the clip applier.

SUMMARY OF THE INVENTION

A non-limiting embodiment of the present invention provides a trigger lockout device for a clip applying instrument, the clip applying instrument having a squeezable trigger, a barrel having a plurality of serially-installed clips therein, and a pair of jaws operatively connected to the trigger and configured to crimp a clip of the plurality of serially-installed clips. The lockout device includes a displaceable slider actuable by squeezing the trigger and configured to slide in first and second directions within the barrel in a longitudinal axial direction, a block disposed within the barrel. When a first number of the plurality of serially-installed clips have not been applied and when the trigger is squeezed, the slider slidably engages and displaces the block and slides along a path in the axial direction to retrieve a clip of the first number of the plurality of serially-installed clips, and to insert the clip into the pair of jaws, and when a second number of the plurality of serially-installed clips have not been applied, the second number being between and including zero and a number less than the first number, the slider engages the block to substantially prevent the slider from sliding along the path in at least one of the first or second directions such that the trigger substantially cannot be unsqueezed.

In a feature of the invention, when the second number the plurality of serially-installed clips have not been applied, the slider engages the block to substantially prevent the slider from sliding along the path in the first and second direction such that the trigger substantially cannot be squeezed or unsqueezed.

In another feature, the instrument further includes a ladder member disposed in the barrel, the ladder member having a plurality of rungs and a solid surface, the ladder member configured to slide in the axial direction and engage a rearmost clip of the plurality of serially-installed clips. When the first number of the plurality of serially-installed clips have not been applied, the slider may displace the block between rungs of the ladder member and out of the path, and when the second number of the plurality of serially-installed clips have not been applied, the solid surface may prevent the slider from being displaced, such that the slider engages the block to substantially prevent the slider from sliding along the path in at least one of the first or second direction such that the trigger substantially cannot be unsqueezed.

In a further feature, the instrument further has a spine substantially axially disposed within the barrel, the spine having an aperture configured to accept the insertion of a portion of the block therein, the slider is configured to slide along the path against an underside the spine, the block is connected to the underside of the spine, and the ladder member is configured to slide in the axial direction above the spine. Also, a flexible rod which connects the block to the spine may be provided. Additionally, the slider may include a tooth configured to engage the block. Also, at least one of the tooth or the slider may have an angled engagement surface.

In another feature, the ladder member and the plurality of serially-installed clips are disposed within a cartridge that is removable from and insertible into the barrel, and the slider is configured to disengage from the block when the cartridge is removed from the barrel.

A feature also may provide a method for operating a clip applying instrument, the clip applying instrument having a squeezable trigger, a barrel having a block and plurality of serially-installed clips therein, a slider disposed within the barrel and operatively connected to the trigger, and a pair of jaws operatively connected to the trigger. The method may include squeezing the trigger to proximally slide the slider along a path in a generally longitudinal axial direction in relation to the barrel, releasing the trigger to distally slide the slider along the path such that the slider engages and displaces the block, inserting a clip of the plurality of clips between the pair of jaws, again squeezing the trigger to crimp the clip between the pair of jaws and to again proximally slide the slider along the path, again releasing the trigger such that the slider engages the block to substantially prevent the slider from sliding in at least one of the proximal or distal directions and such that the trigger substantially cannot be unsqueezed.

In another feature, again releasing the trigger further includes the slider engaging the block to substantially prevent the slider from sliding in the proximal and distal directions. In a further feature, the instrument may include a ladder member disposed in the barrel, the ladder member having a plurality of rungs and a solid surface, and the squeezing of the trigger may further include sliding the ladder member in the axial direction and engage a rearmost clip of the plurality of serially-installed clips, the releasing of the trigger may further include displacing, with the slider, the block between rungs of the ladder member and out of the path, and the again releasing of the trigger may further include preventing, with the solid surface, the slider from being displaced, such that the slider engages the block to substantially prevent the slider from sliding along the path in at least one of the first or second direction such that the trigger substantially cannot be unsqueezed. Also, the releasing of the trigger may further include displacing at least a portion of the block through the aperture. In a further feature, the method further includes inserting the cartridge into the barrel, and disengaging the slider from the block when the cartridge is removed from the barrel.

Another feature of the invention provides a clip applying instrument including a squeezable trigger, a barrel configured to accept a plurality of serially-installed clips therein, a pair of jaws operatively connected to the trigger and configured to crimp a clip of the plurality of serially-installed clips, a displaceable slider actuable by squeezing the trigger and configured to slide along a path in first and second directions within the barrel in a longitudinal axial direction, and a block disposed within the barrel, wherein when a first number of the plurality of serially-installed clips have not been applied and when the trigger is squeezed, the slider slide engages and displaces the block and slides along a path in the axial direction to retrieve a clip of first number of the plurality of serially-installed clips, and to insert the clip into the pair of jaws, and when a second number of the plurality of serially-installed clips have not been applied, the second number being between and including zero and a number less than the first number, the slider engages the block to substantially prevent the slider from sliding along the path in at least one of the first or second directions such that the trigger substantially cannot be unsqueezed.

In an additional feature, a ladder member may be disposed in the barrel, the ladder member having a plurality of rungs and a solid surface, the ladder member configured to slide in the axial direction and engage a rearmost clip of the plurality of serially-installed clips, when the first number of the plurality of serially-installed clips have not been applied, the slider is configured to displace the block between rungs of the ladder member and out of the path, when the second number of the plurality of serially-installed clips have not been applied, the solid surface prevents the slider from being displaced, such that the slider engages the block to substantially prevent the slider from sliding along the path in at least one of the first or second direction such that the trigger substantially cannot be unsqueezed.

The may further include a spine substantially axially disposed within the barrel, the spine having an aperture configured to accept the insertion of a portion of the block therein, wherein the slider is configured to slide along the path against an underside the spine, the block is connected to the underside of the spine, and the ladder member is configured to slide in the axial direction above the spine.

Additionally, the ladder member and the plurality of serially-installed clips may be disposed within a cartridge that is removable from and insertible into the barrel, and the slider may be configured to disengage from the block when the cartridge is removed from the barrel.

Other exemplary embodiments and advantages of the present invention may be ascertained by reviewing the present disclosure and the accompanying drawings, and the above description should not be considered to limit the scope of the present invention.

BRIEF DESCRIPTION OF THE DRAWINGS

The present invention is further described in the detailed description which follows, in reference to the noted plurality of drawings, by way of non-limiting examples of preferred embodiments of the present invention, in which like characters represent like elements throughout the several views of the drawings, and wherein:

FIG. 45 is an enlarged perspective sectional view of an indicating arrangement according to an embodiment of the present invention in a generally fully-crimped position.

DETAILED DESCRIPTION OF THE PREFERRED EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
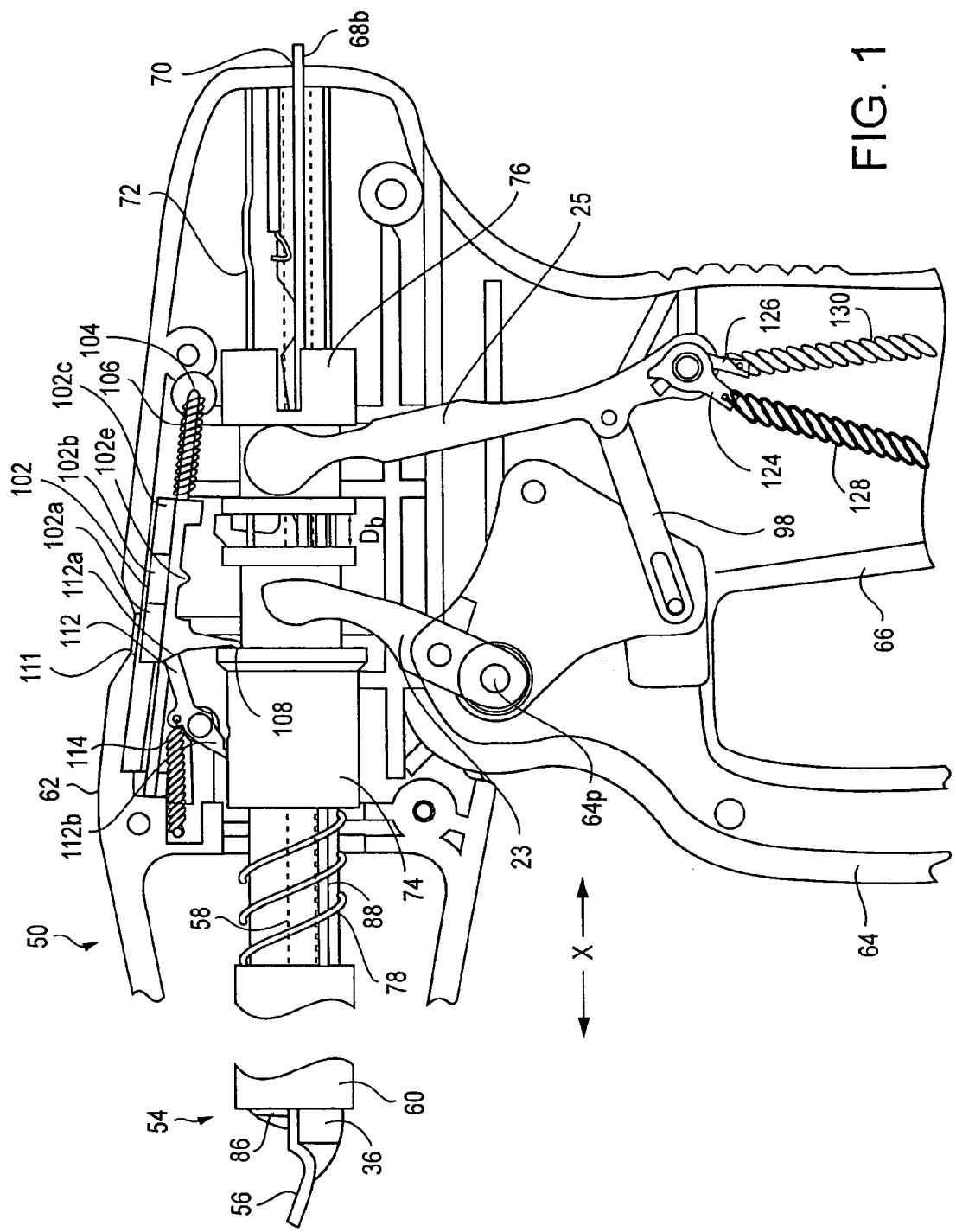
FIG. 1 is a sectional view of a medical clip applying device according to an embodiment of the present invention, showing a large cartridge inserted therein.
Figure 4:
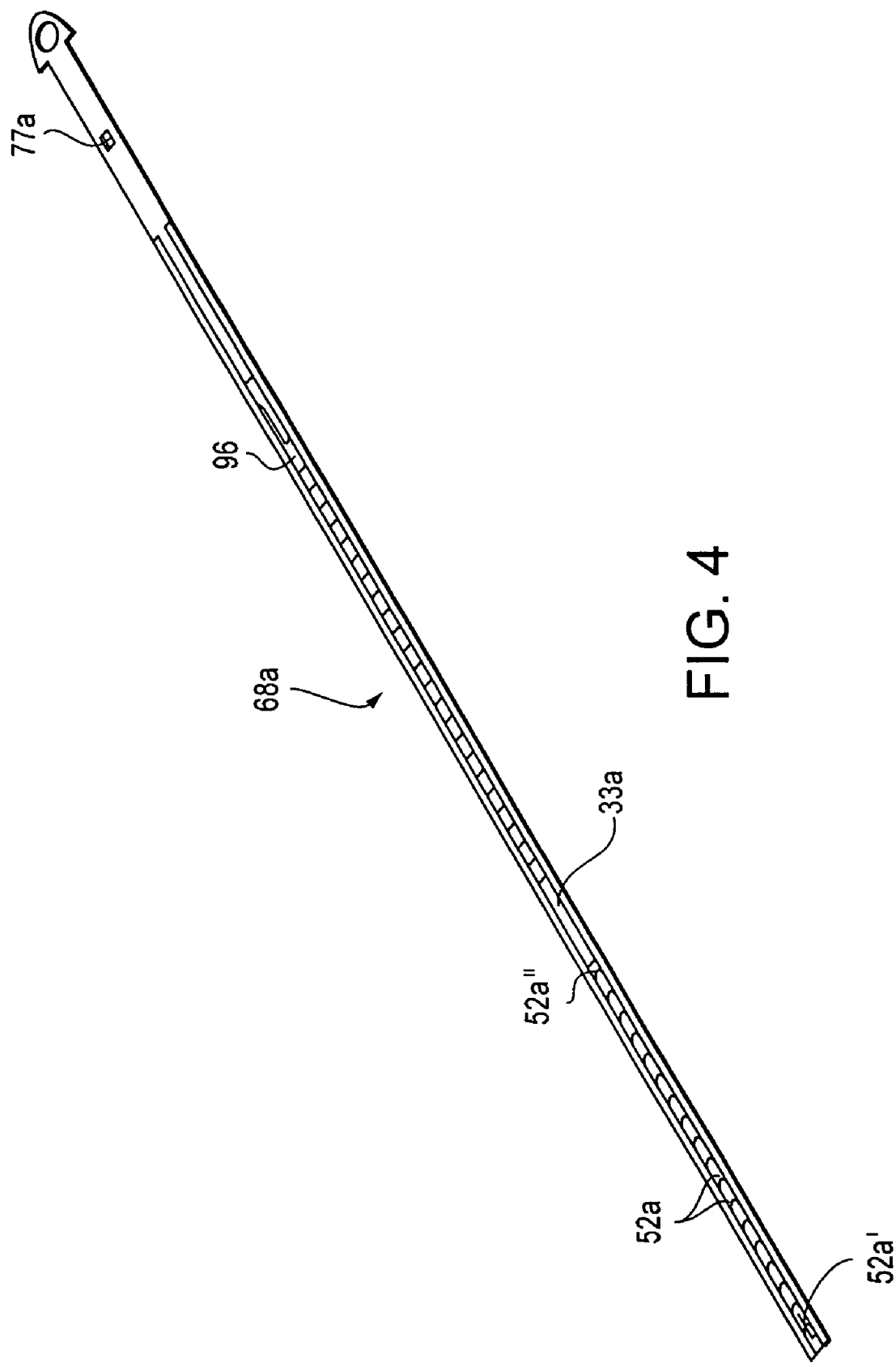
FIG. 4 is a perspective view of a medium-large clip supply cartridge for use with an embodiment of the present invention.
Figure 5:
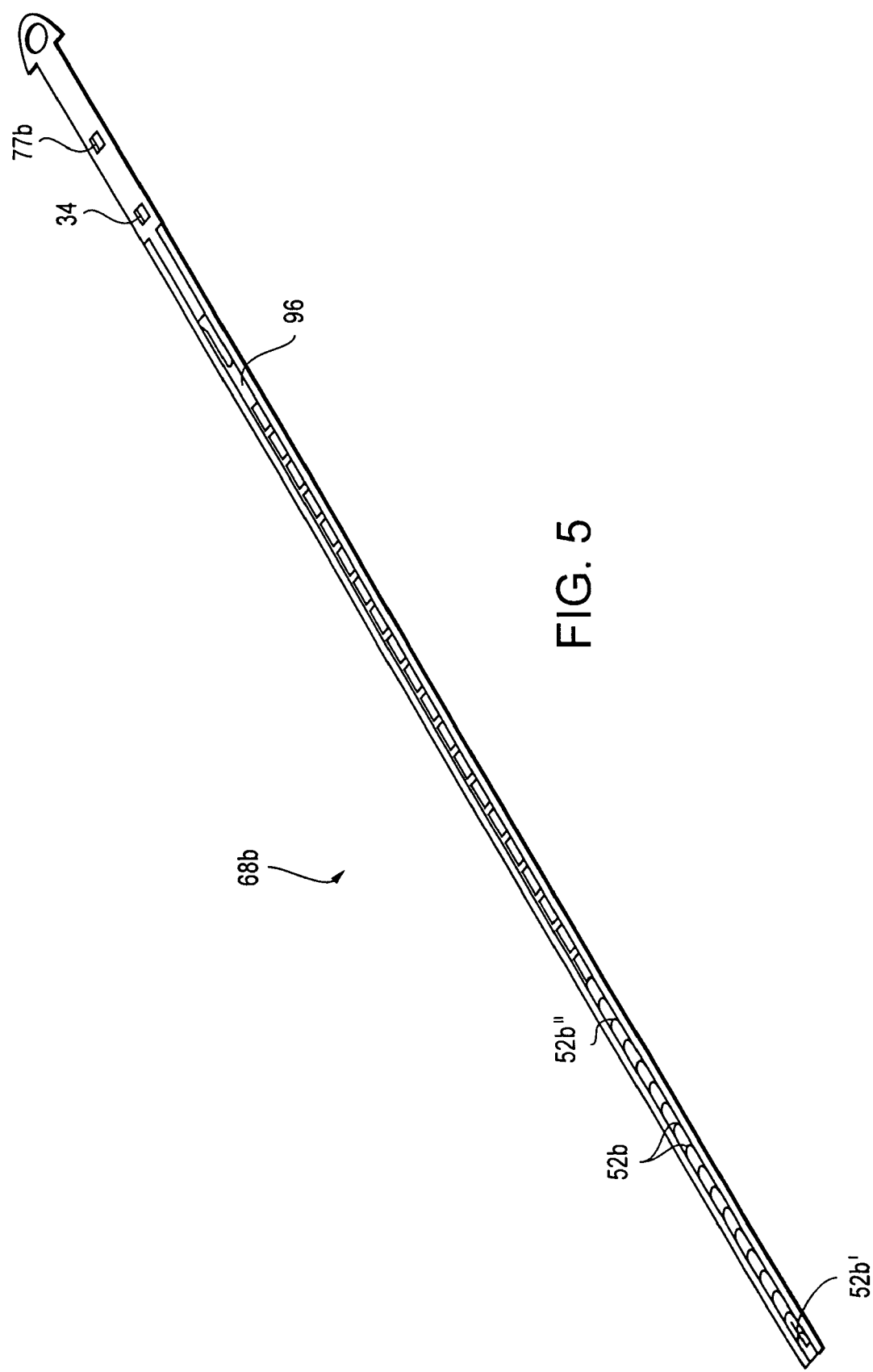
FIG. 5 is a perspective view of a large clip supply cartridge for use with an embodiment of the present invention.
Figure 6:
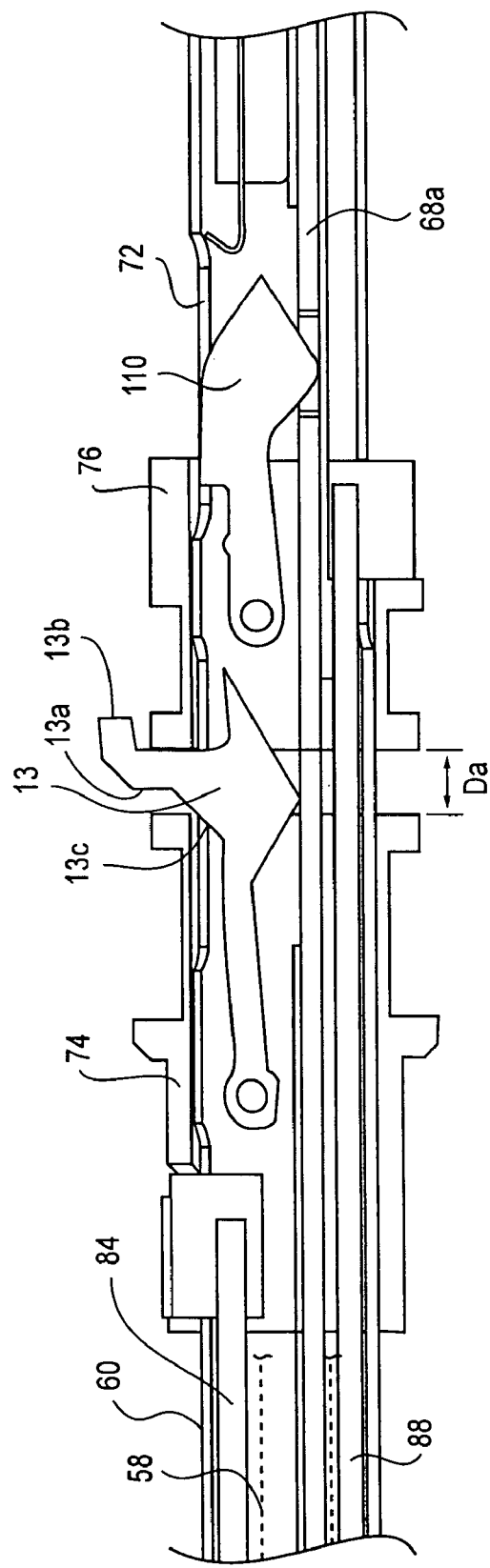
FIG. 6 is a side sectional view of an elongated tube of an embodiment of the present invention, showing a medium-large clip supply cartridge inserted therein.
Figure 7:
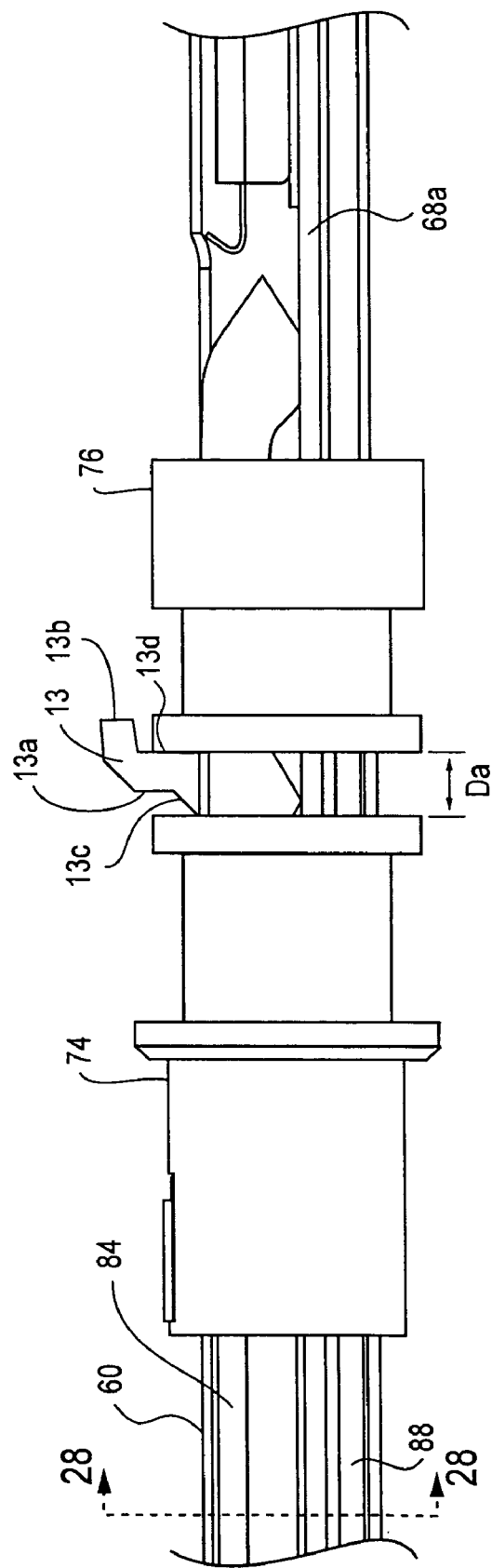
FIG. 7 is another side sectional view of an elongated tube of an embodiment of the present invention, showing a medium-large clip supply cartridge inserted therein.
Figure 8:
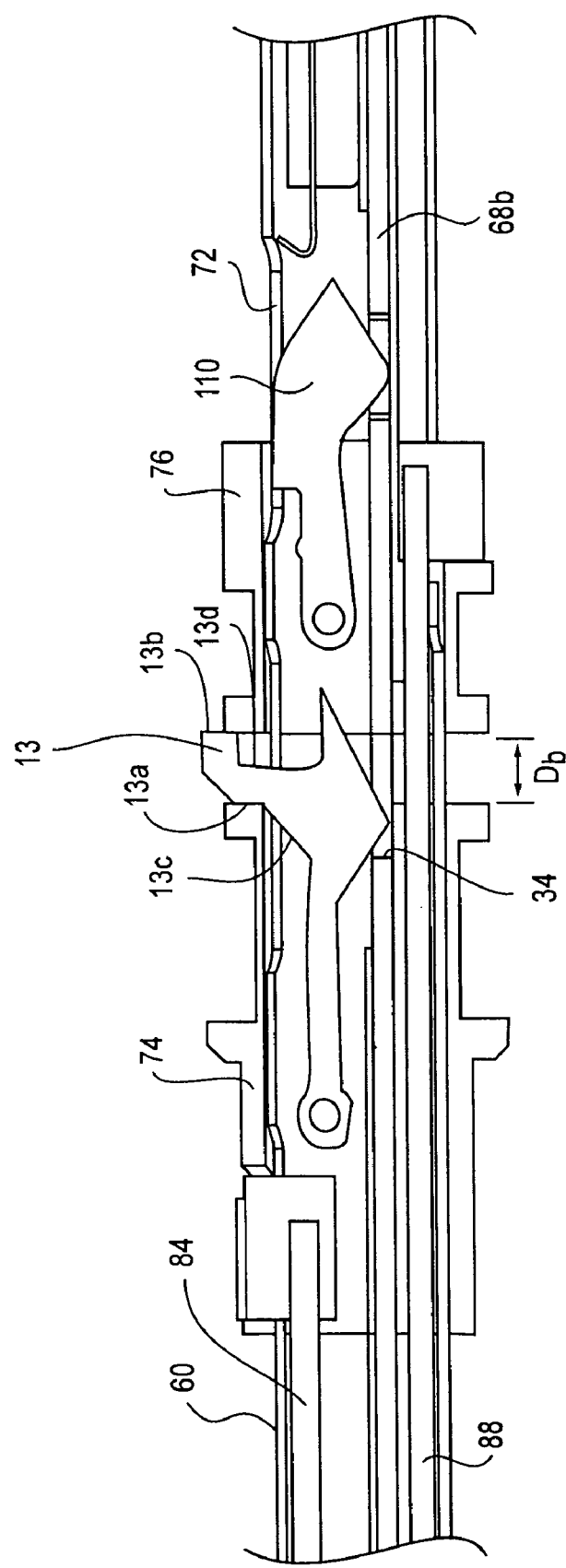
FIG. 8 is a side sectional view of an elongated tube of an embodiment of the present invention, showing a large clip supply cartridge inserted therein.
Figure 9:
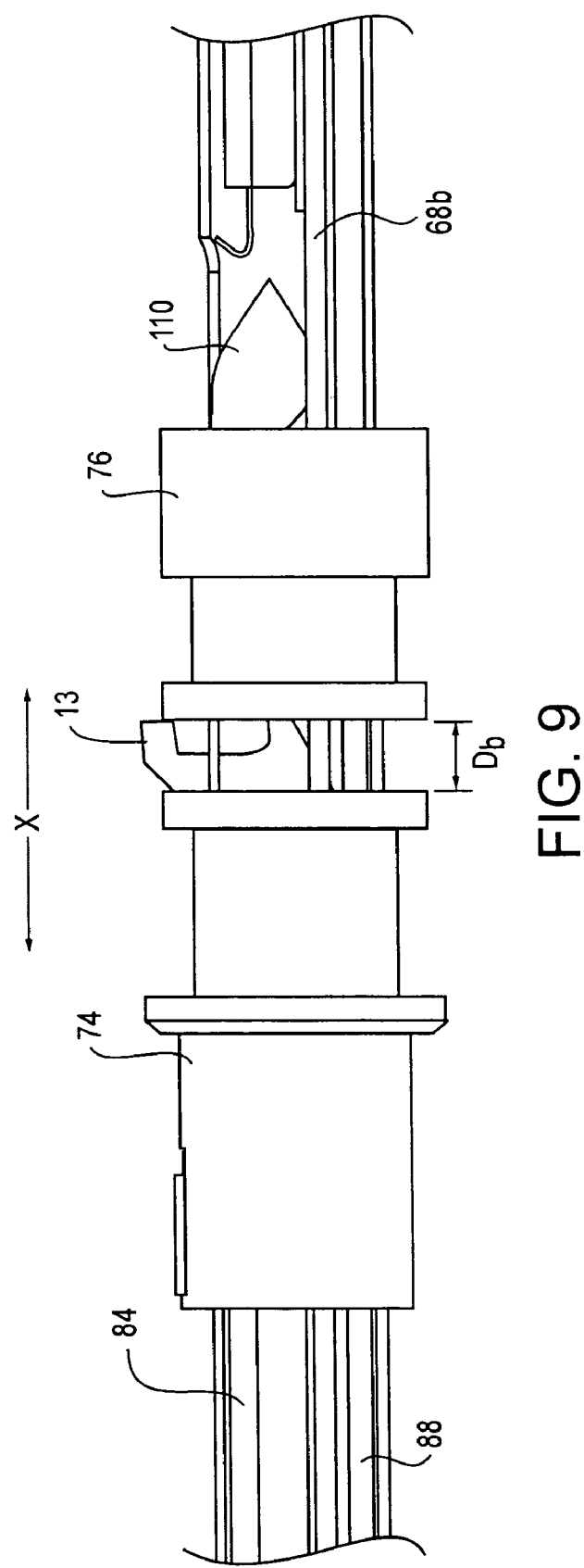
FIG. 9 is another side sectional view of an elongated tube of an embodiment of the present invention, showing a large clip supply cartridge inserted therein.

Referring to the drawings, wherein like characters represent like elements, FIG. 1 shows a clip applying device 50 for applying medical tissue-pinching clips 52a, 52b to tissue. The clip applying device 50 has a patient-engaging distalmost end 54 with a pair of squeezable jaw members (jaws) 56 arranged thereon. An elongated channel member or frame (also referred to as the spine) 58 is surrounded by an elongated tube 60, which elongated tube 60 and elongated channel member 58 are secured at their respective proximalmost ends to the distal end of a generally pistol-like handle grip assembly 62. The handle grip assembly 62 includes an arcuately movable squeezable trigger 64 that pivots about pivot shaft 64P. By releasing the squeezed trigger 64 away from a housing portion 66 of the handle grip assembly 62, a clip 52a (shown in FIG. 2), 52b (shown in FIG. 3) is advanced through the distal end of the elongated channel member 58 and into the jaws 56 from an elongated ladder-like clip supply cartridge 68a (shown in FIG. 4), 68b (shown in FIG. 5), disposed through the elongated channel 58. The elongated clip supply cartridge 68a, 68b is fed into a receiving slot or port 70 in the proximal end of the handle grip assembly 62, the receiving slot being in communication with the elongated channel 58.

A rotatable enclosure barrel (also referred to as a tube) 72 is rotatably supported within the handle grip assembly 62. The rotatable enclosure barrel 72 is connected to the proximal end of the elongated channel 58. The enclosure barrel 72 has an annular distal bearing (first bearing) 74 slidably disposed thereon and an annular proximal bearing (second bearing) 76 slidably disposed thereon. While the figures show a cylindrical barrel (i.e., a round cross-section), it should be readily appreciable by those skilled in the art that the barrel may have alternative shapes, including but not limited to oval, square and triangular cross sections. The distal bearing 74 has a compression spring 78 arranged against its distalmost surface 80. The compression spring 78 releases a cinch 86 after the jaws 56 have been closed and a clip 52a, 52b has been crimped, and also provides a proximally-directed bias against the distal bearing 74.

The distal bearing 74 has an elongated cinch rod 84 (shown in FIGS. 6-9) extending distally therefrom. The cinch rod 84 extends through the length of the elongated channel 58 (and its surrounding protective enclosure tube 60). The cinch 86 (shown in FIG. 10) is generally semi-cylindrically-shaped and arranged on the distal end of the cinch rod 84. The cinch 86 is slidably arranged on the distal end of the elongated channel 58 and is reciprocally slidable in axial direction X to engage the jaws 56 which are squeezably arranged on the distal end of the clip applying device. The each jaw member 56 is located on a respective jaw arm 256, and the jaws 56 and jaw arms are part of a jaw assembly 156. The jaw arms 256 are biased outwardly (i.e., the jaws 56 are biased open). Distal and proximal movement of the cinch 86 in axial direction X and with respect to the elongated channel 58 effects the respective squeezing closure and biased opening of the jaws 56 at the distal end of the elongated channel 58. The cinch rod 84 moves in axial direction X to slide the cinch 86 distally and proximally corresponding to the direction of movement of the distal bearing 74 on the distal end of the enclosure barrel 72.

The distal bearing 74 is biased proximally by the compression spring 78, effecting a proximal motion to the distal bearing 74. The distal bearing 74 is operatively connected to the trigger 64 by a distal paddle 23, and the proximal bearing 76 is operatively connected to a proximal paddle 25, which is in turn connected to the trigger by a trigger linkage 98. Thus, the proximal bearing 76 is biased distally by the compression spring via the trigger linkage 98.

Figure 19:
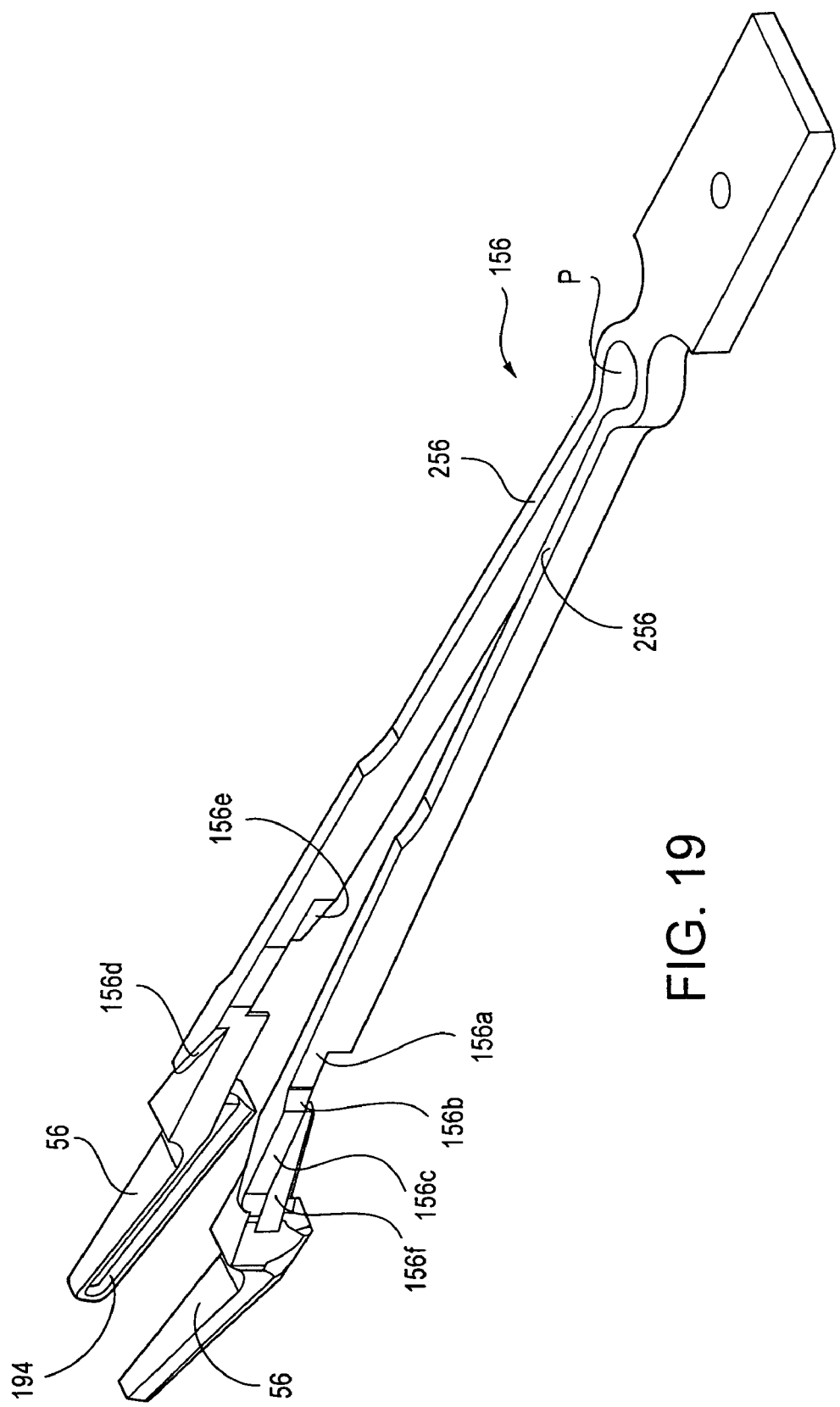
FIG. 19 is an isometric view of the jaw assembly of an embodiment of the present invention.

An elongated pusher rod 88 extends adjacent to the lower side of the elongated channel 58 (as shown, e.g., in FIGS. 1, 6-9 and 37). The elongated pusher rod 88 has a proximal end connected to the proximal bearing 76 surrounding the enclosure barrel 72 at the proximal end of the handle grip assembly 62. The pusher rod 88 is connected to a clip-engaging feeder 90 (shown in FIGS. 2-3). The feeder 90 is movable in axial direction X in relation to the clip-loaded cartridge 68a, 68b disposed within the elongated channel 58; however, the pusher rod is disposed below the elongated channel 58 (shown in FIG. 6). Proximal motion of the feeder 90 is effected by proximal motion of the proximal bearing 76 around the enclosure barrel 72 within the handle grip assembly 62. As the trigger 64 is squeezed (i.e., as the trigger is moved toward the housing portion 66 and pivoted about pivot shaft 64P), the pusher rod 88 distally retracts in the axial direction X due to distal movement of the distal bearing 74, which distally moves feeder 90 to retrieve a distalmost clip 52a', 52b' of the plurality of clips that are serially loaded in respective clip cartridges 68a, 68b, in order to prepare (upon release of the trigger) to load the distalmost clip 52a', 52' into guide slots 194 (shown in FIGS. 10-11 and 19), in the opposed faces of the respective jaws 56. The term "plurality" as used throughout the specification is to be interpreted to mean greater than one and within a number understood by those skilled in the art.

The trigger 64 is biased toward the unsqueezed position by the compression spring 78 (shown in FIG. 1). Upon release of the trigger 64, the distal bearing 74 is biased to move proximally, resulting in proximal (rearward) movement of the cinch 86 by the proximal movement of the cinch rod 84, which permits the jaws 56 to bias themselves open, and the feeder 90 (pushed by the pusher rod 88) to push the next available (distalmost) clip 52a', 52b' into the guide slots 194 of the respective jaws 56 as the jaws 56 open fully, as the trigger 64 is permitted to open fully (shown in FIG. 1) from the housing 66 portion of the handle grip assembly 62. Release of the trigger 64 (after the trigger 46 has been initially squeezed towards the handle 66) will automatically advance the next available distalmost clip 52a', 52b' within the cartridge 68a, 68b.

The embodiments disclosed herein are configured to accept more than one type of cartridge (e.g., cartridges having different sizes and/or shapes). It is noted that throughout the specification, the term "size" to describe the different clips and/or the cartridges also includes shape as well. In a non-limiting embodiment, the clip applying device 50 of present invention accepts a clip cartridge 68a containing a series of medium-large sized clips 52a, and can also accept a clip cartridge 68b containing a series of large-sized clips 52b. It should be readily appreciable by those skilled in the art, however, that in alternative embodiments, the present invention may be configured to accept various other types of clip cartridges, including but not limited to small and medium cartridges, medium and medium-large cartridges, and small and large cartridges. Additionally, while the figures show the clip applying device 50 being able to work with two types of cartridges, it should be readily appreciable by those skilled in the art, however, that in alternative embodiments more than two types of cartridges may be accepted.

Referring to FIGS. 6-9, when the clip applying device 50 is loaded with a cartridge 68a, 68b, there is a predetermined distance Da, Db between the proximal bearing 76 and distal bearing 74, this distance being determined by a stop key 13 located in the enclosure barrel 72.

When the clip cartridge 68b is inserted into the receiving slot or port 70 of the clip applying device 50, the cartridge is slid along axial direction X until it reaches a stop (not shown) and the cartridge can no longer be slid. The stop key 13 is then lowered into a stop keyhole 34 (shown in FIG. 5) of the cartridge 68b by pivoting action of the stop key (shown in FIGS. 8-9). When the trigger 64 is released (i.e., when the clip applying device 50 is at rest, shown in FIG. 1), the proximal bearing 76 and distal bearing 74 move towards each other such that the stop key 13 is sandwiched therebetween to create a distance Db between the proximal bearing and distal bearing. The distance Db results from the distal bearing 74 contacting a first distal face 13a of the stop key 13, and the proximal bearing 76 contacting a first proximal face 13b of the stop key.

When the clip cartridge 68a is inserted by the user into the receiving slot or port 70 of the clip applying device 50, the cartridge slides along axial direction X until it reaches a stop and the cartridge can no longer move axially. The clip cartridge 68a (shown in FIG. 4) does not have a stop keyhole for the lowering of the stop key 13 therein. Thus, when the trigger 64 is released (i.e., when the clip applying device 50 is at rest), the proximal bearing 76 and distal bearing 74 move towards each other such that the stop key 13 is sandwiched therebetween to create a distance Da between the proximal bearing and distal bearing (shown in FIGS. 6-7). The distance Da results from the distal bearing 74 contacting a second distal face 13c of the stop key 13, and the proximal bearing 76 contacting a second proximal face 13d of the stop key. The distance Da is less then the distance Db because the proximal bearing 76 and distal bearing 74 are closer to each other in the axial direction X.

Figure 2:
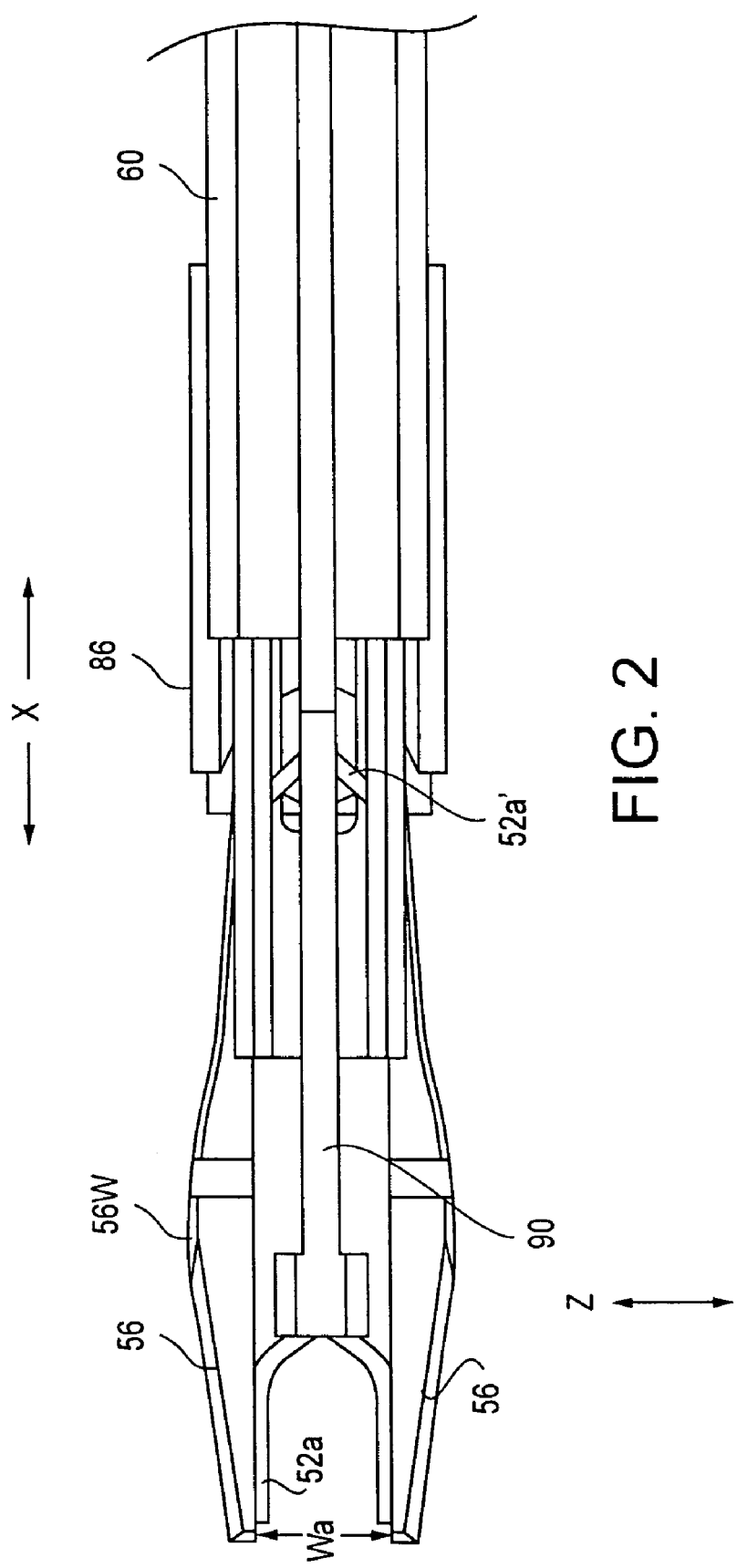
FIG. 2 is a bottom plan view of a distal end of the medical clip applying device, showing a medium-large clip inserted therein.
Figure 3:
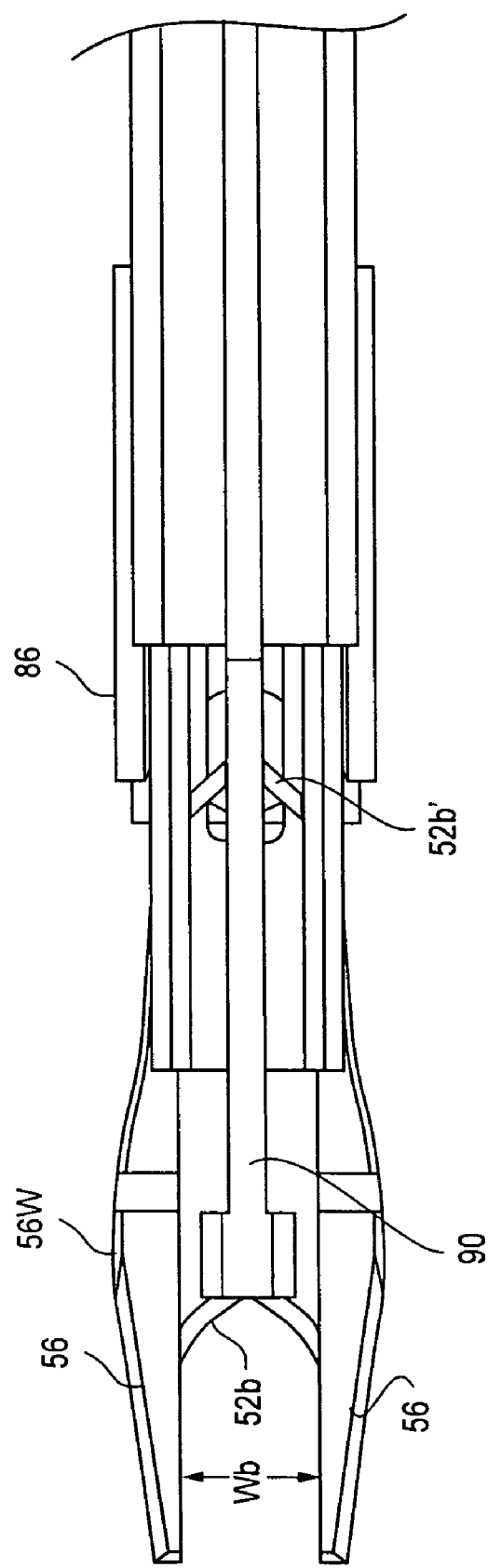
FIG. 3 is a bottom plan view of a distal end of the medical clip applying device, showing a large clip inserted therein.

Additionally, due to the configuration of the face surfaces 13a-d of the stop key, when the cartridge 68a is inserted into the clip applying device 50, the proximal bearing 76 and distal bearing are both located more distally than when the cartridge 68b is inserted into the clip applying device. Thus (as shown in FIG. 2-3), when the cartridge 68a is inserted into the clip applying device 50, the cinch is advanced in the distal direction to narrow the jaws to a width Wa, and when the cartridge 68b is inserted into the clip applying device 50, the cinch 86 is advanced (a lesser amount than when the cartridge 68a is inserted) in the distal direction to narrow the jaws to a width Wb. The width Wa is narrower than the width Wb because when the cartridge 68a is inserted into the clip applying device, the cinch 86 is distally advanced a greater amount in the axial direction X than when the cartridge 68b is inserted into the clip applying device. As described further hereinbelow, each jaw member 56 is increasingly tapered from a proximal point along the axial direction X to a distalward point where a maximum width portion 56W is located. Thus, the more the cinch 86 is advanced distally toward the maximum width portion 56W, the narrower the width between the jaws. In this way (shown in FIG. 2), the narrower width Wa allows the jaws 56 to securely accommodate medium-large clips 52a in the guide slots 194.

Similarly (shown in FIG. 3), when the cartridge 68b is inserted into the clip applying device 50, since the cinch 86 is advanced a lesser amount than when the cartridge 68a is inserted, the jaws are opened wider to width Wb to allow the jaws 56 to securely accommodate large clips 52b in the guide slots 194, which may have a width larger than smaller clips (e.g., medium-large clips 52a).

Further (as shown in FIG. 2-3), when the cartridge 68a is inserted into the clip applying device 50, the feeder 90 is advanced to the proper position to load the clip 52a, and when the cartridge 68b is inserted into the clip applying device 50, the feeder 90 is advanced (a lesser amount than when the cartridge 68a is inserted) to properly load the larger clip 52b. In other words, when the cartridge 68b is inserted, the feeder 90 does not distally advance as much as when the cartridge 68a is inserted, because the feeder must be further back to accommodate the larger clip 52b (shown in FIG. 3), which may have a longer length than smaller clips (e.g., medium-large clips 52a).

In the above-described embodiment, the position in the axial direction X of both the cinch 86 and the feeder 90 is determined by the stop key 13; however, it is appreciable by those skilled in the art that in alternative embodiments, the position in the axial direction X of only one of the cinch 86 and the feeder 90 may be determined by the stop key, i.e., the stop key may be differently configured to allow varied displacement between the proximal bearing 76 and distal bearing 74. For example, when two clip types of different widths but of the same lengths are respectively used in two different cartridge types, the displacement in the axial direction X of only the cinch may be varied depending on which cartridge type is used, because the feeder is displaced by the same amount in either clip type. Similarly, when two clip types of different lengths but of the same widths are respectively used in two different cartridge types, the displacement in the axial direction X of only the feeder may be varied depending on which cartridge type is used, because the distance between the jaws does not need to be adjusted.

It is noted that in a non-limiting embodiment, either or both cartridges 68a, 68b may contain safety keyholes 77a and 77b (shown in FIGS. 4-5) which do not interact with the stop key 13, but rather accept a safety key 110, in order to prevent insertion or withdrawal of the clip cartridge 68a, 68b unless the trigger 64 is generally fully squeezed rearwardly toward the handle 66 of the handle grip assembly 62 in a manner similar to that disclosed in commonly-assigned U.S. Patent Publication No. 2003/0040759.

It is also noted that in a non-limiting embodiment, the trigger 64 may be squeezed to allow the insertion of the cartridge 68a, 68b and/or to crimp a clip 52a, 52b; however, it should be appreciated that in alternative embodiments, other structure may be used (e.g., a separate or integral tab, button, lever or switch), which may be activated to allow the cartridge 68a, 68b to be inserted (and/or to crimp a clip 52a 52b), such that the position in the axial direction X of the proximal bearing 76 or the distal bearing 74 may be determined.

The cinch 86 and jaw assembly 156 of the present invention allow full, positive and consistent control of the opening and closing of the jaws 56 in direction Z (shown in FIGS. 2 and 10), hereinafter referred to as radial movement, or movement in the radial direction. Because the clip applying device 50 is able to accept two different types of clip cartridges 68a, 68b, and the jaws 56 thus move radially over a greater distance than other clip appliers, such full, positive and consistent control of the jaws 56 is required. Further, limited travel in the axial direction X of a cinch is normally not enough to cover this increased radial travel of the jaws 56. In other words, there is no single surface of the cinch 86 or jaw assembly 156 to completely and accurately control the opening and closing of the cinch.

Figure 13:
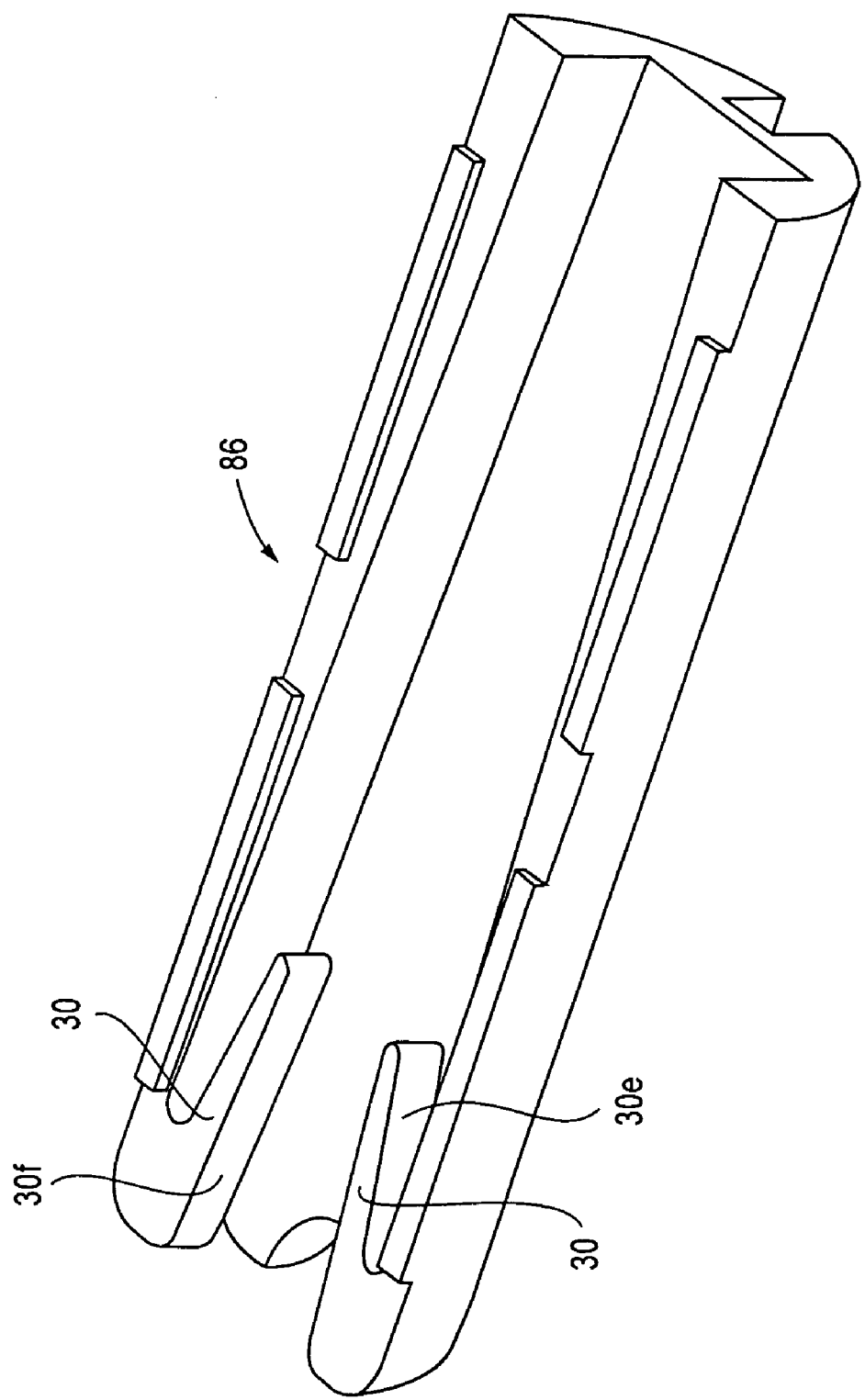
FIG. 13 is a perspective view of the underside of a cinch of an embodiment of the present invention.

An embodiment of the present invention includes a cinch 86 that allows for greater radial movement of the jaws 56 by engaging different jaw engagement surfaces 156a, 156b, 156c, 156d, 156e, 156f of each jaw arm 256. The generally semi-cylindrically-shaped cinch 86 has a pair of control fingers (or control members) 30 (shown in FIG. 13) on the underside thereof which engage inner engagement surfaces 156e and outer engagement surfaces 156f of the jaw arms. In a non-limiting embodiment, the inner and outer engagement surfaces 156e, 156f, as well as the control fingers 30, may be tapered or angled.

Figure 14:
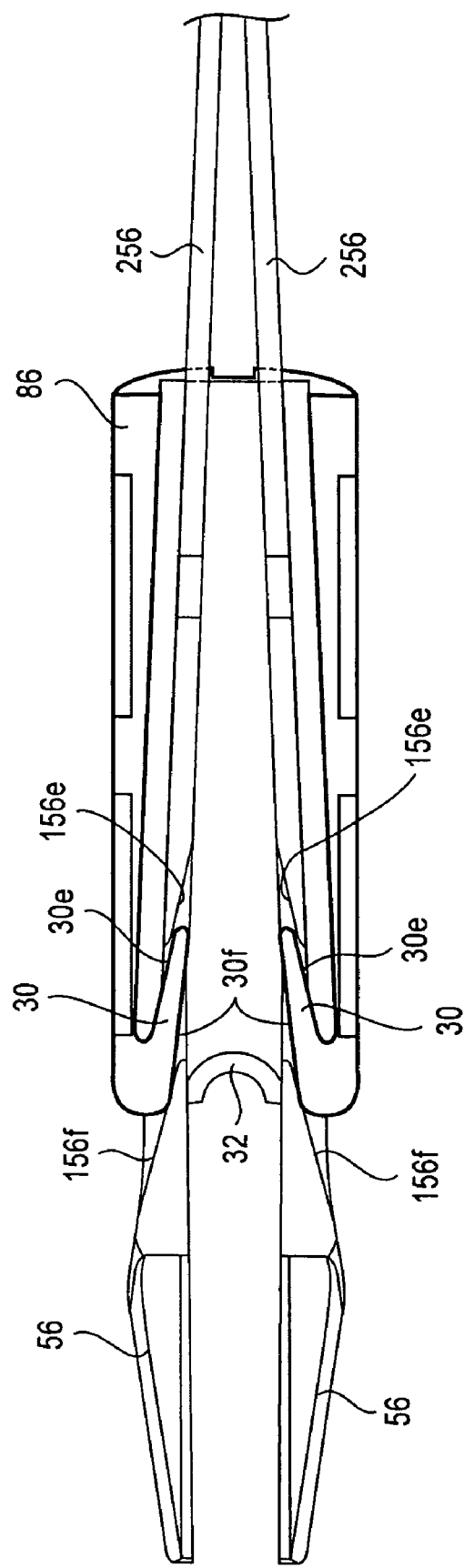
FIG. 14 is a perspective view of the underside of the cinch in an intermediate position.

FIG. 14 shows the cinch 86 in an intermediate position, where the control fingers 30 are intermediate the respective inner engagement surfaces 156e and outer engagement surfaces 156f. In this position (in a non-limiting embodiment), medium-large clips 52a may be loaded and the jaw arms may be at rest (i.e., spring forces of the jaw arms are acting neither inwardly nor outwardly in the radial direction Z).

Figure 15:
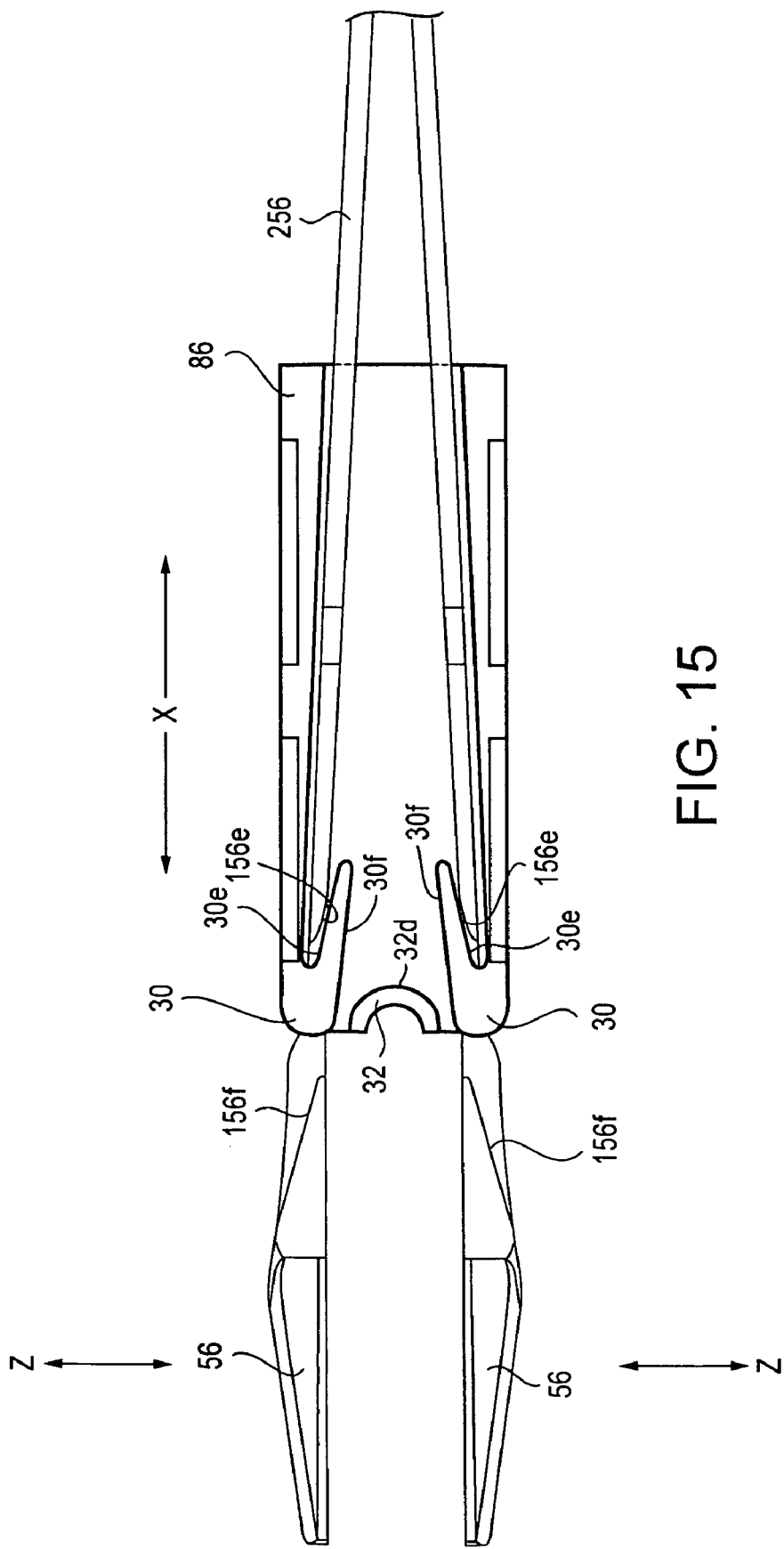
FIG. 15 is a plan view of the underside of the cinch of an embodiment of the present invention, in a proximal position.
Figure 17:
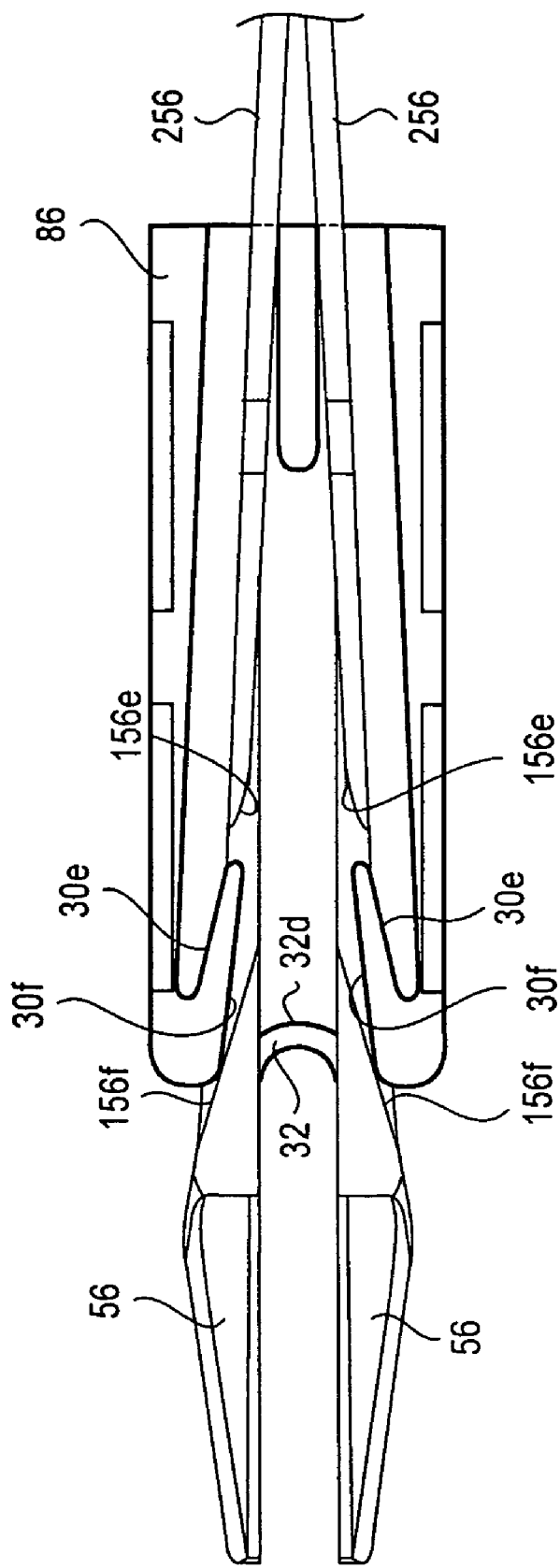
FIG. 17 is a plan view of the underside of the cinch and jaw assembly of an embodiment of the present invention, when the jaws are in a partially-closed position.

When the cinch is moved proximally in the axial direction X from the intermediate position, outer control surfaces 30e of the control fingers 30 respectively engage the inner engagement surfaces 156e to widen the gap between the jaws 56 (e.g., to a width Wb, in order to accommodate cartridge 68b containing large sized clips 52b), while inner control surfaces 30f of the control fingers are brought out of contact with respective outer engagement surfaces 156f, as shown in FIGS. 15 and 17. Conversely, when the cinch is moved distally from a proximalmost position toward the intermediate position, the outer control surfaces 30e of the control fingers respectively slide along the inner engagement surfaces 156e to gradually (due to the angled configuration) let the jaw arms 256 bias themselves inward.

Similarly, when the cinch is moved distally in the axial direction X from the intermediate position, inner control surfaces 30f of the control fingers 30 respectively engage the inner engagement surfaces 156e to narrow the gap between the jaws 56 (e.g., to a width Wa, to accommodate cartridge 68a containing medium-large sized clips 52a, or to begin a clip-crimping operation), while outer control surfaces 30e of the control fingers are brought out of contact with respective outer engagement surfaces 156e, as shown in FIGS. 15 and 17. In a non-limiting embodiment, in order to ensure smooth transfer of control throughout the range of movement of the cinch 86, the control fingers 30 are preferably always in contact with at least one of the inner or outer engagement surfaces 156e, 156f (as shown in FIG. 14).

Figure 16:
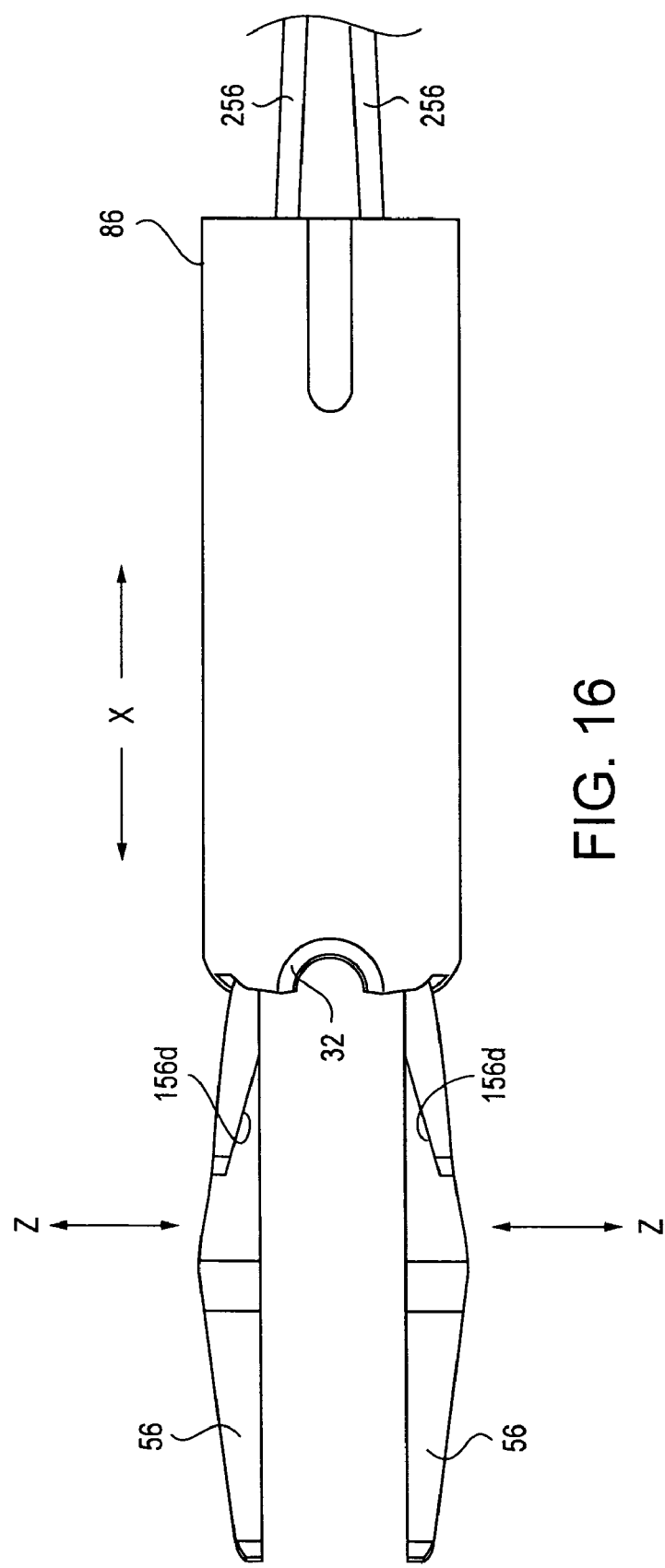
FIG. 16 is a top plan view of the of the cinch of an embodiment of the present invention, in the proximal position.
Figure 18:
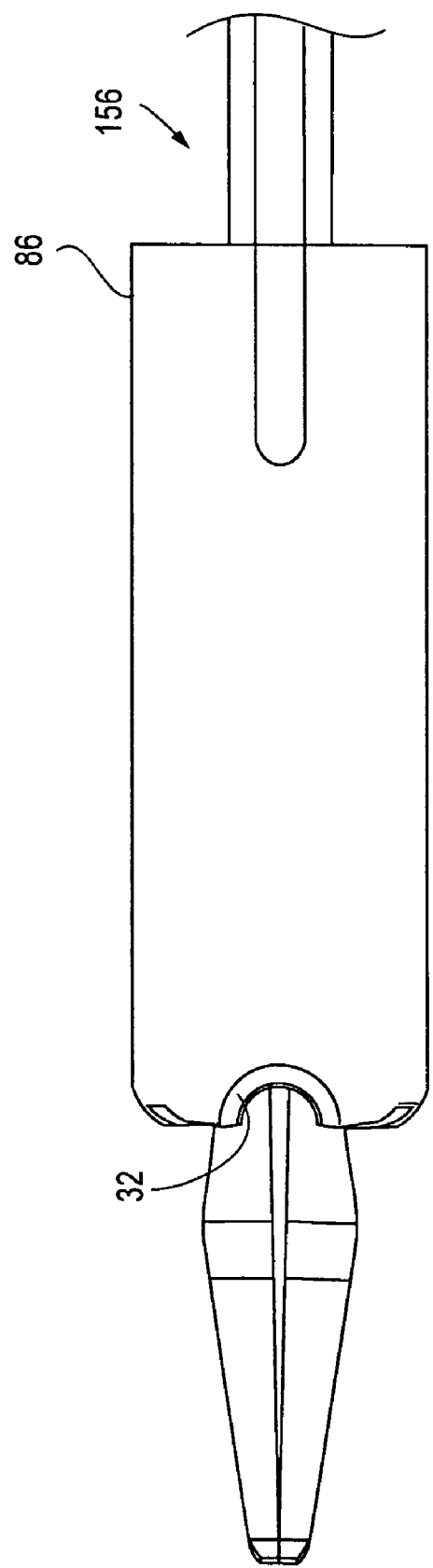
FIG. 18 is a plan view of the jaw assembly and cinch of an embodiment of the present invention, when the jaws are in a closed position.

FIG. 18 shows the cinch 86 in a fully distal position in which a clip 52a, 52b may be fully crimped closed. In a non-limiting embodiment, in order to move the cinch 86 from the fully-distal position along the axial direction X, the cinch includes a generally arcuate central block 32 having opposed ends which respectively engage second inner engagement surfaces 156d located on an upper surface of each jaw arm 256 (shown in FIGS. 16 and 19), which may be tapered or angled in a non-limiting embodiment. The central block 32 ensures accurate and precise transition of the control surfaces of the cinch 86 when the jaws 56 begin to open (i.e. when the cinch moves proximally along axial direction X) from the closed jaw position. For example, when the cinch 86 begins to open from the closed jaw position (shown in FIG. 18), a proximal facing surface 32d of the central block 32 engages the second inner engagement surfaces 156d commence an opening operation of the jaws. After the cinch 86 moves proximally partway along the axial direction X toward the intermediate position, control of the opening of the jaws 56 is "handed off" to the inner control surfaces 30f of the control fingers 30, which respectively slide along the outer engagement surfaces 156f to gradually (due to the angled configuration) provide for outward movement of the jaw arms 256 (in direction Z). Although the central block 32 is shown in the figures as being arcuate, it should be understood by those skilled in the art that the central block may take a variety of shapes, including but not limited to, e.g., a wedge, circle, a V or W shape.

Figure 20:
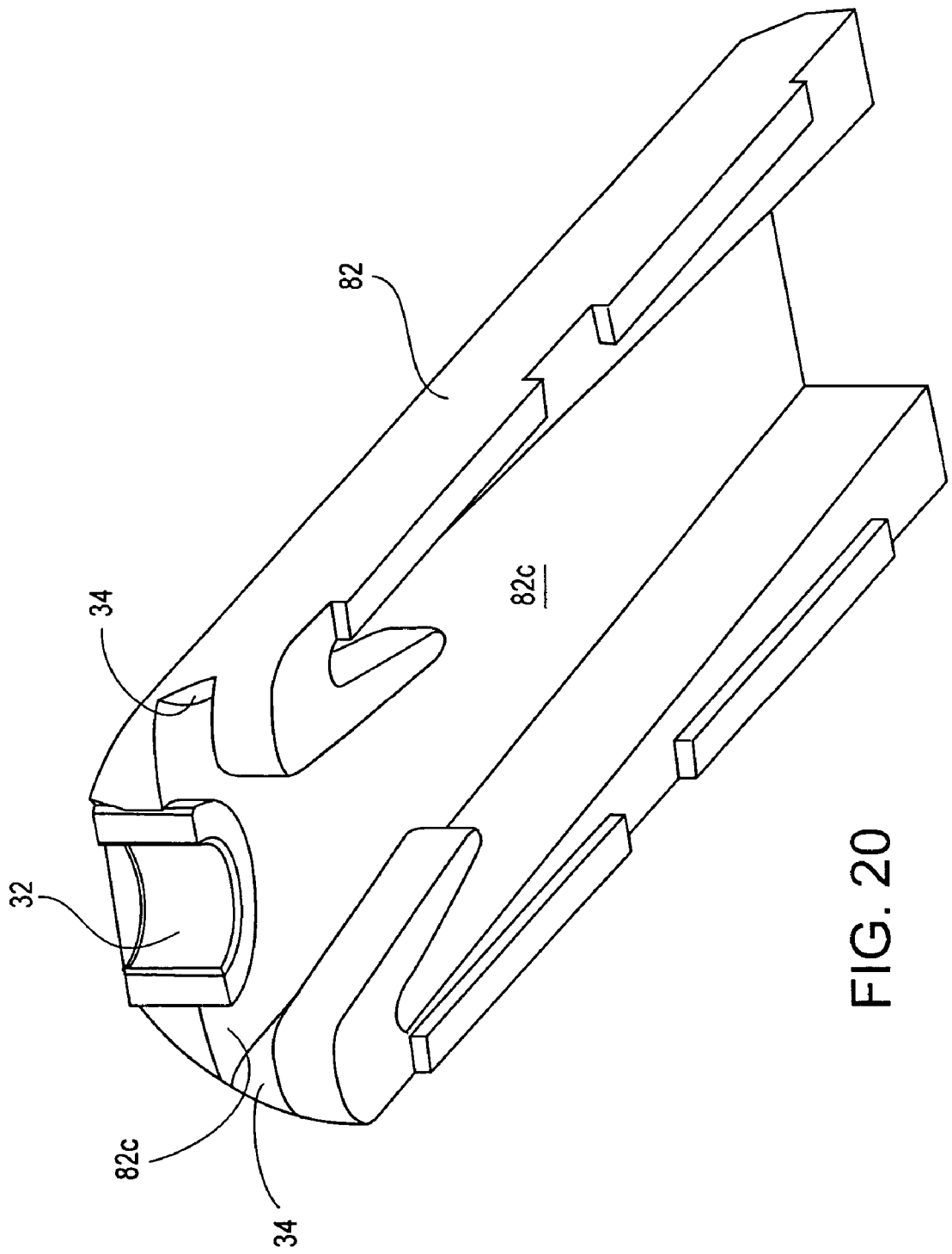
FIG. 20 is an upper isometric view of the cinch of an embodiment of the present invention.
Figure 21:
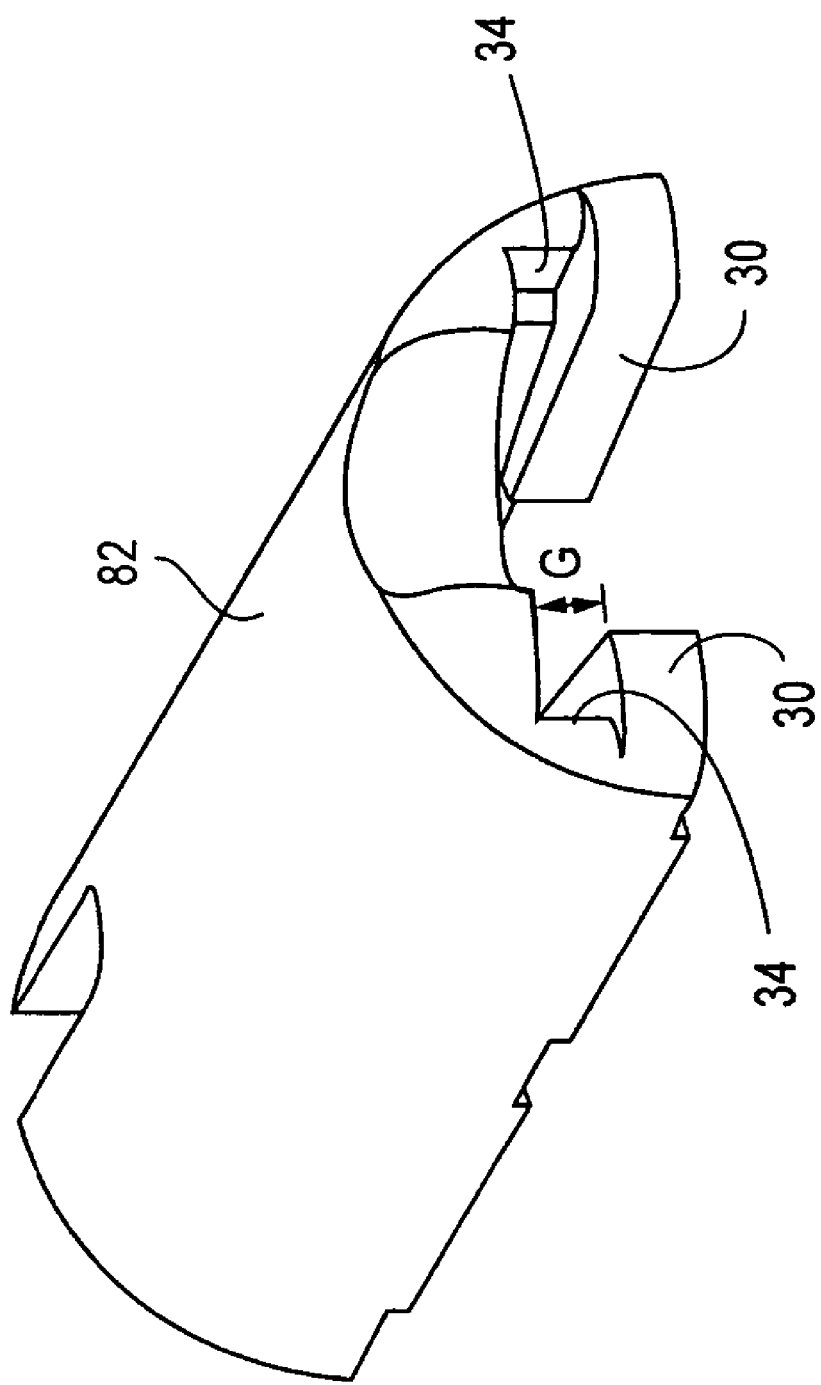
FIG. 21 is a lower isometric view of the cinch of an embodiment of the present invention.
Figure 22:
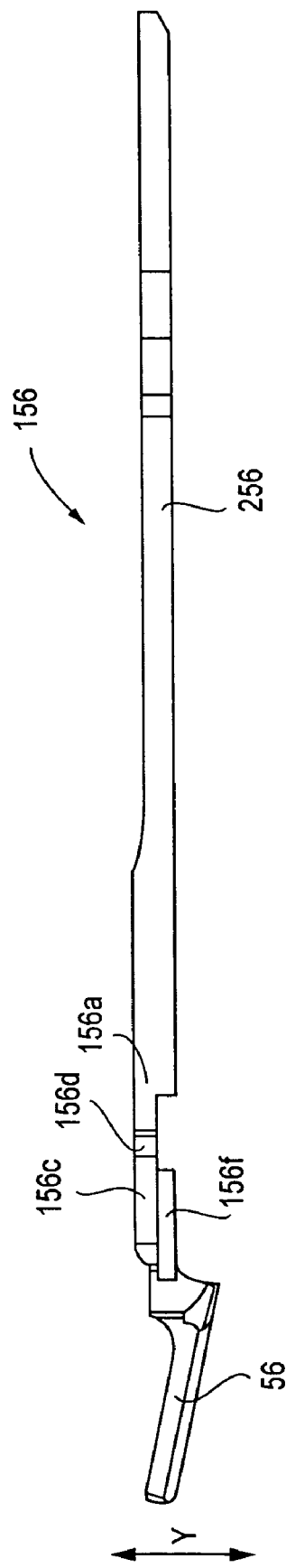
FIG. 22 is a side elevational view of the jaw assembly.
Figure 23:
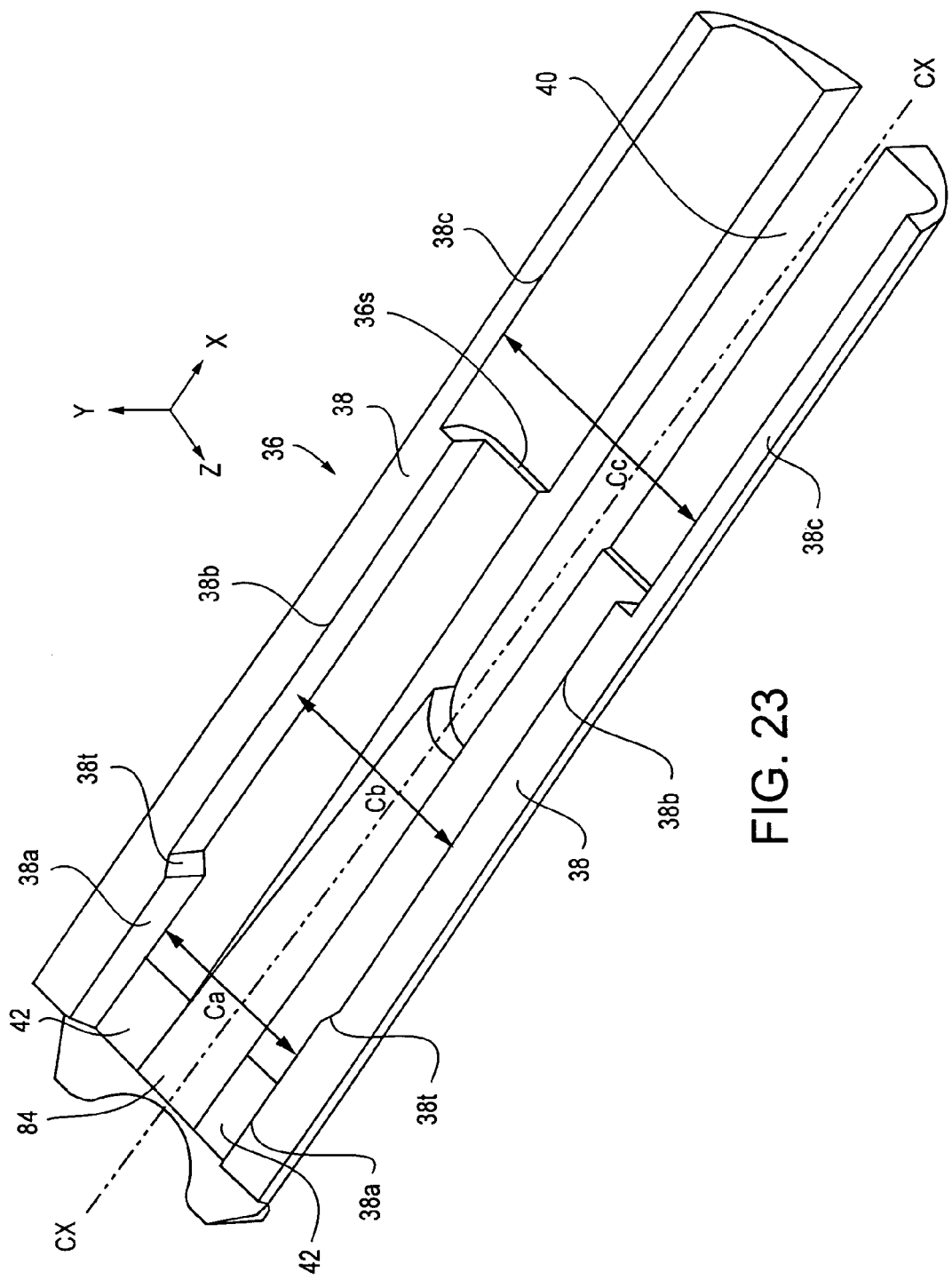
FIG. 23 is a perspective view of a cartridge alignment device of an embodiment of the present invention.
Figure 24:
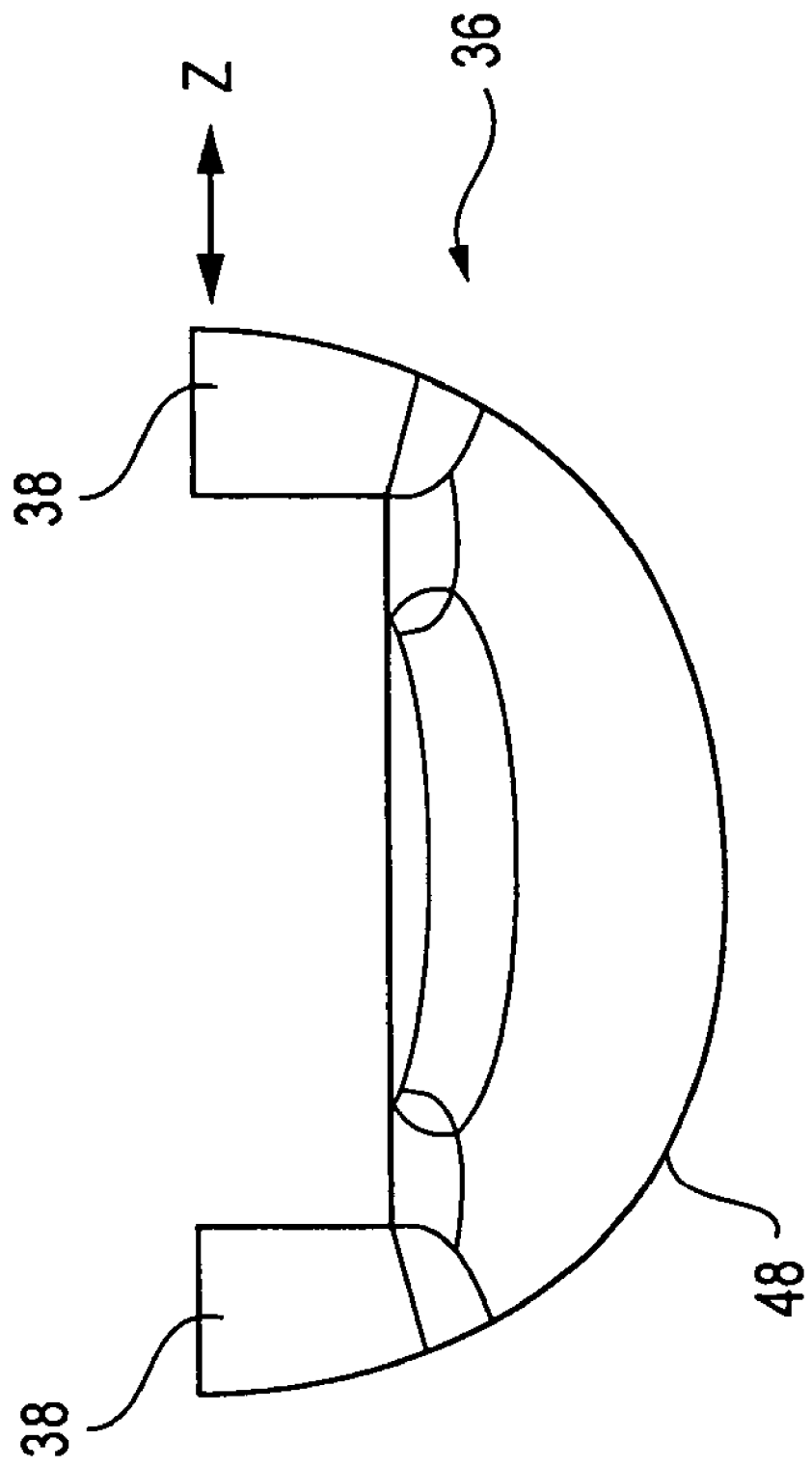
FIG. 24 is a frontal view of the cartridge alignment device of an embodiment of the present invention.
Figure 25:
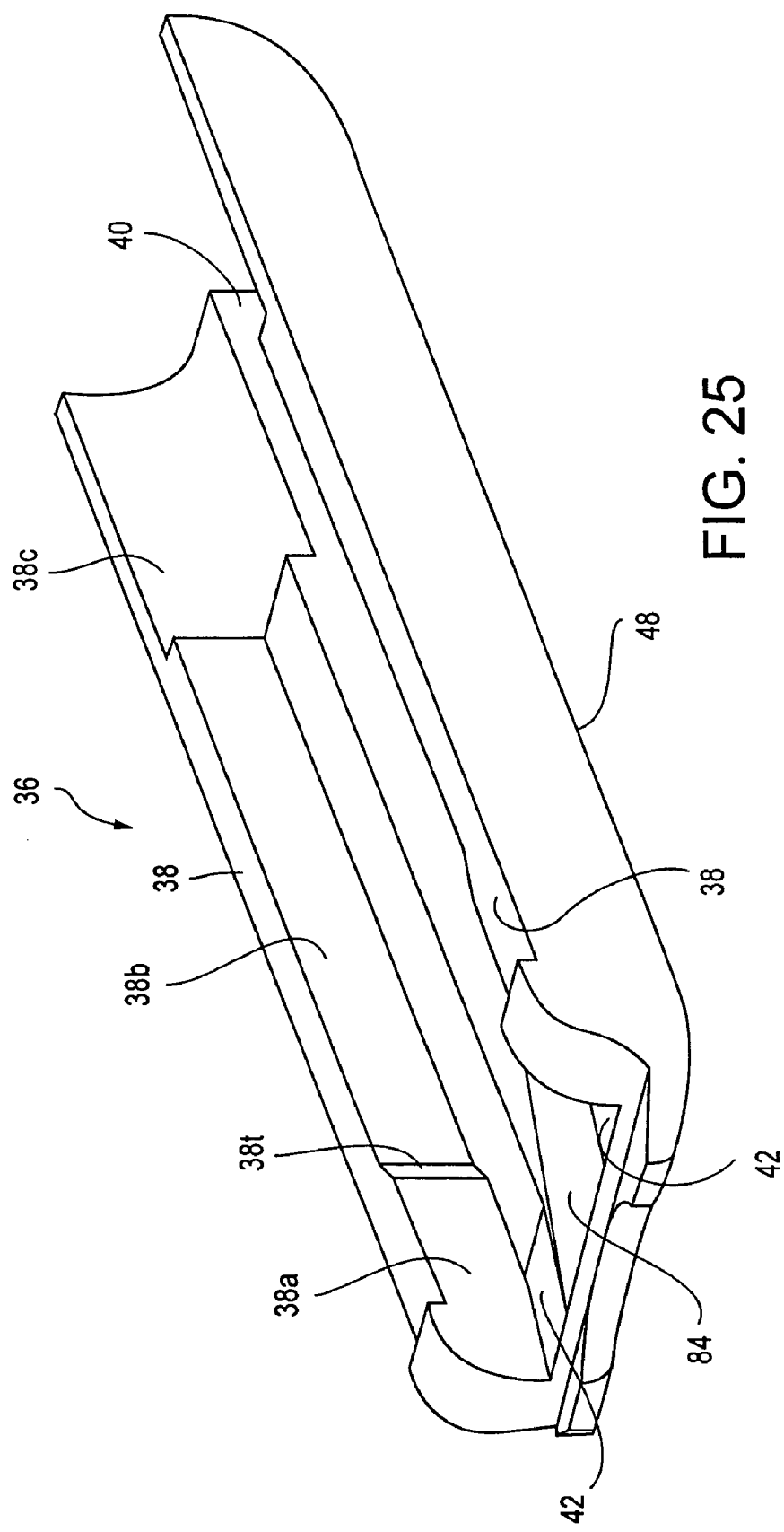
FIG. 25 is another perspective view of the cartridge alignment device of an embodiment of the present invention.
Figure 26:
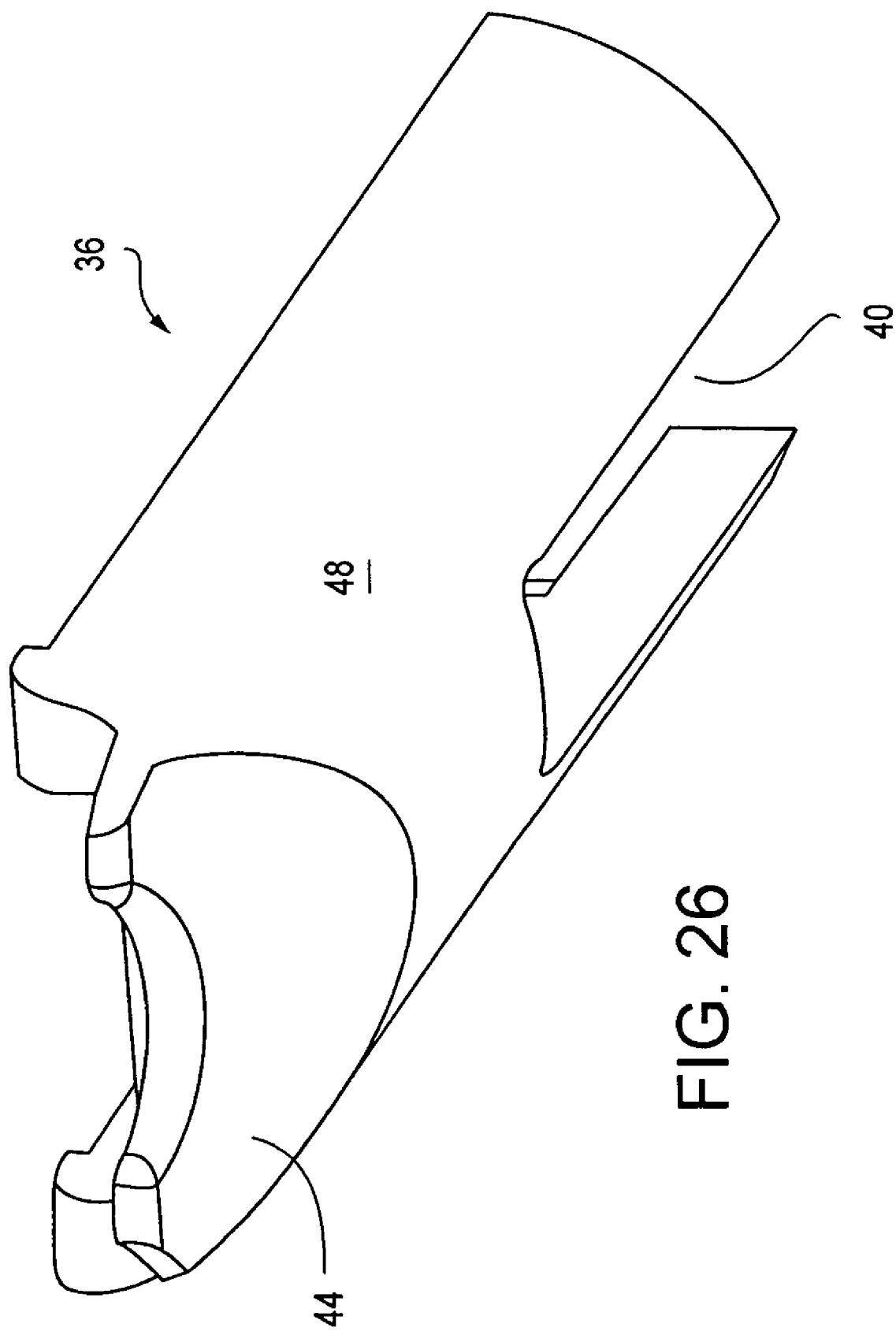
FIG. 26 is a bottom perspective view of the cartridge alignment device of an embodiment of the present invention.
Figure 27:
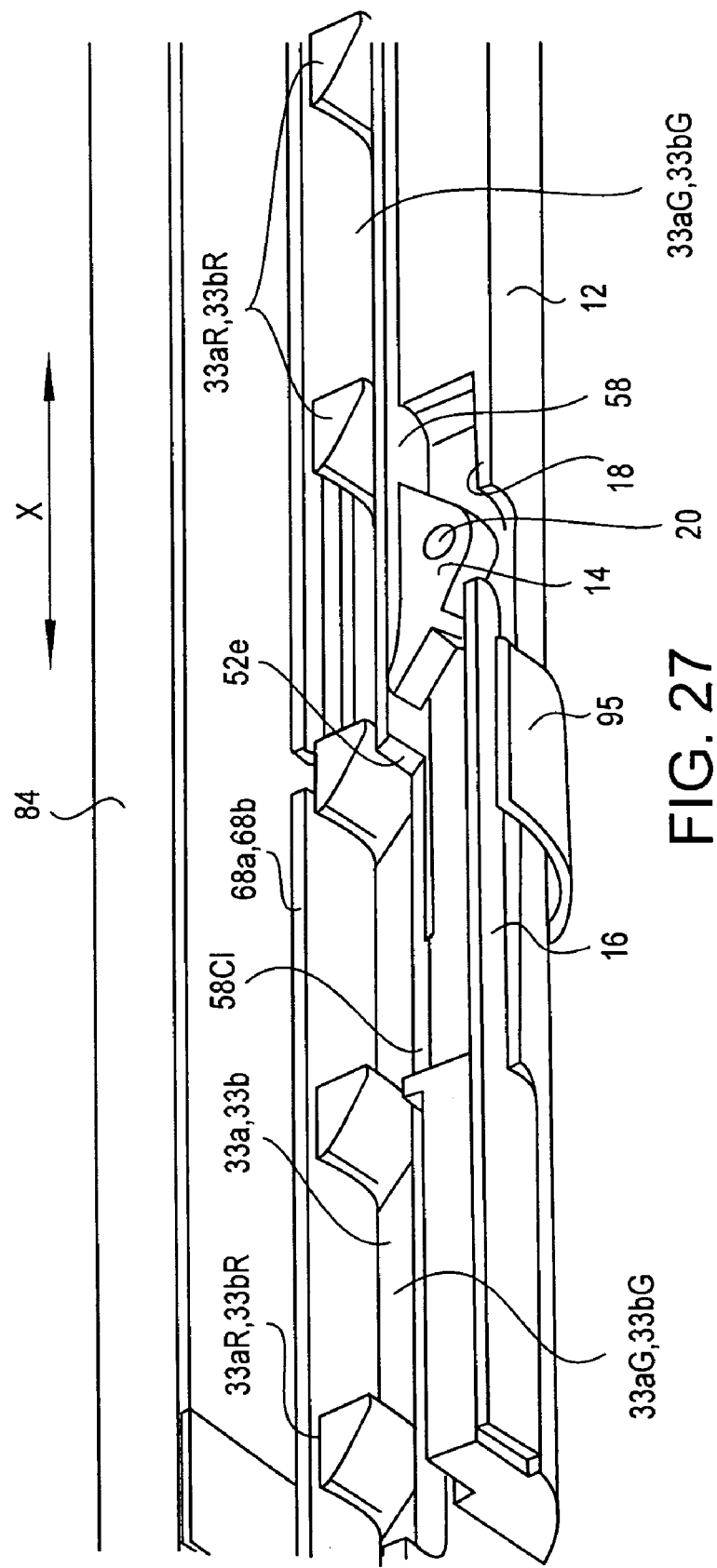
FIG. 27 is a perspective, sectional view of a slider of an embodiment of the present invention.

In a non-limiting embodiment, the cinch 82 may include a pair of inwardly facing guide walls 34 (shown in FIGS. 20-21) configured to respectively slidingly engage one or more outer side engagement surfaces 156a-c (shown in FIGS. 19 and 22) of each jaw arm 256 to provide further control of (e.g., pitch in the radial direction) the jaw assembly 156 by the cinch. With such a configuration it may not be necessary for the jaw assembly 156 to remain at rest in the intermediate position. Additionally, since the control fingers 30 protrude inwardly, a gap or channel G may be present between the control finger 30 and the ceiling 82c of the cinch 82. A portion of each jaw arm 256 may then be sandwiched between a respective control finger 30 and the ceiling 82c of the cinch 82, thereby providing control and stability (by e.g., preventing dive) of the jaws in a Y-axis direction as the cinch slides in the X-axis direction.

Figure 10:
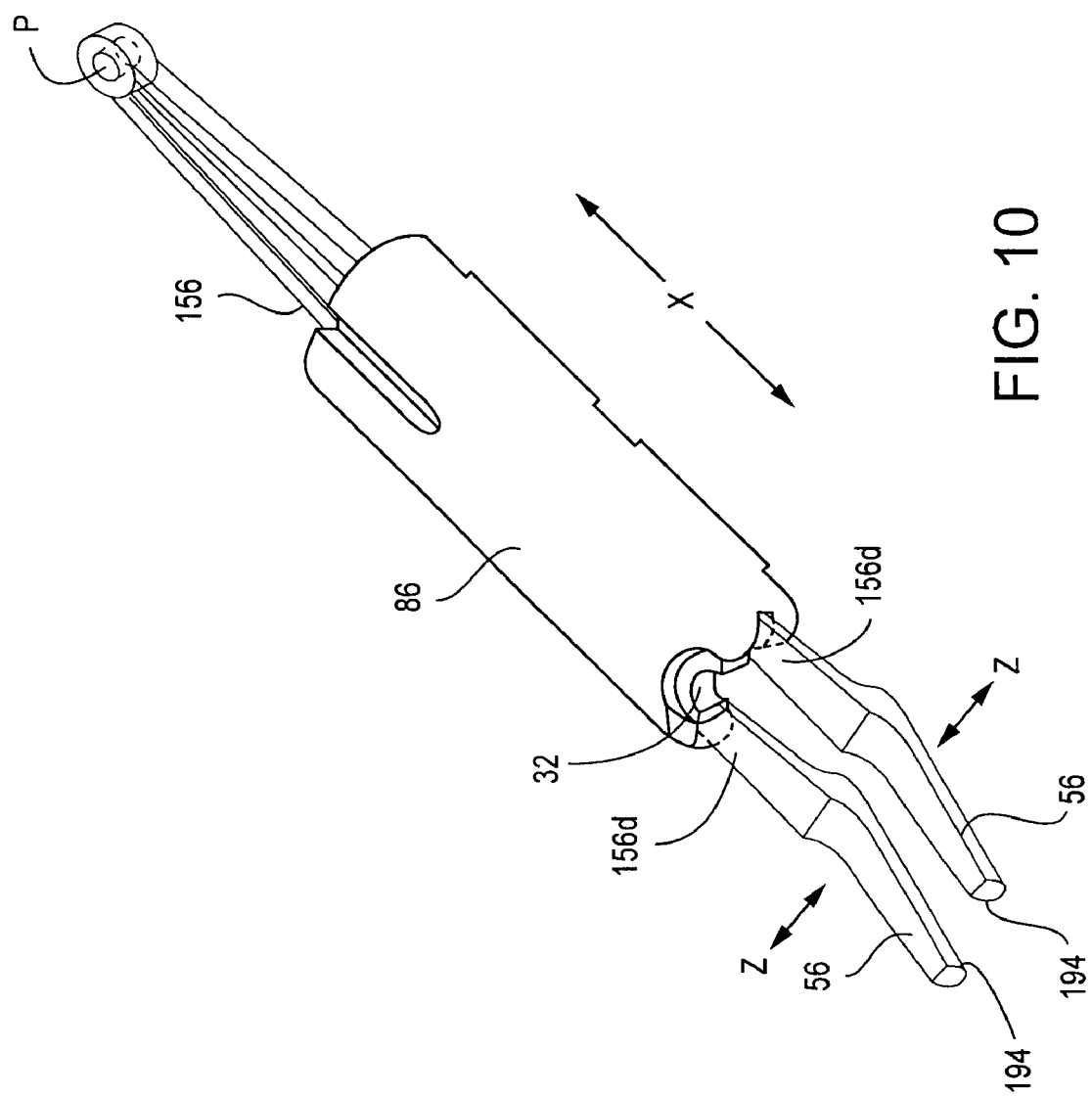
FIG. 10 is a perspective view of a jaw assembly and cinch of an embodiment of the present invention.
Figure 11:
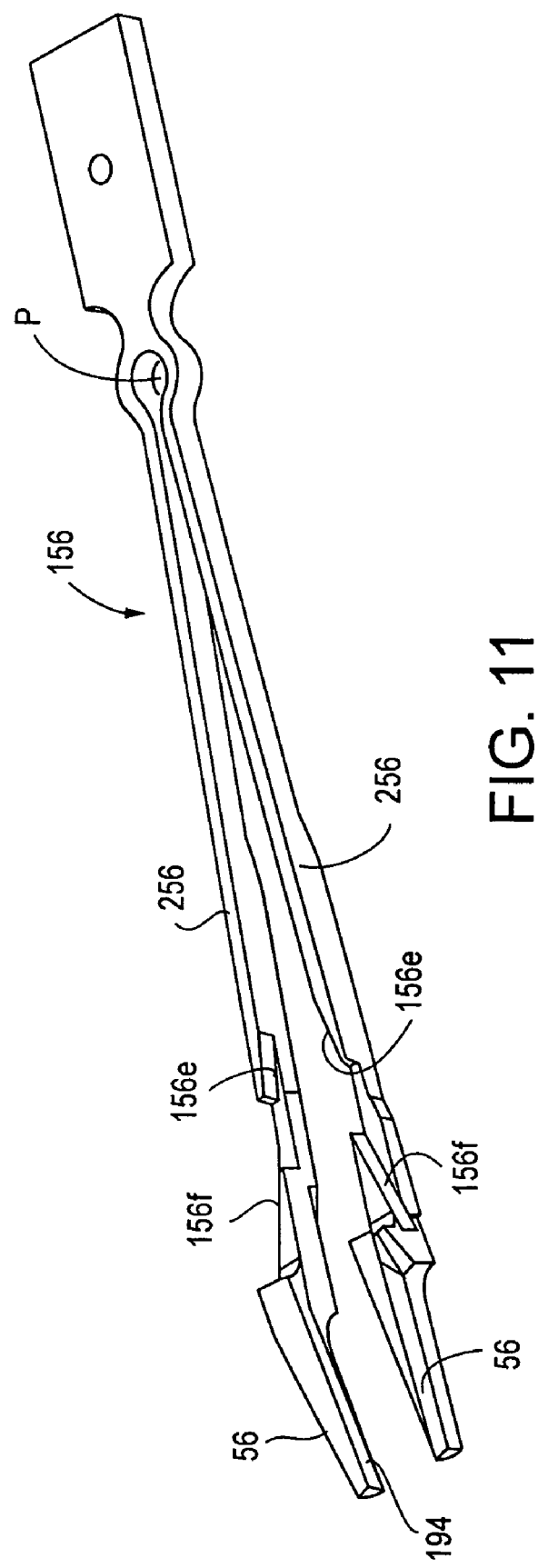
FIG. 11 is a perspective view of the underside of a jaw assembly of an embodiment of the present invention.

In FIGS. 2 and 10, the radial opening and closing direction of the jaws 56 appears to be orthogonal to the axial direction X (i.e., it appears to be parallel to the axial direction Z); however, it should be understood by those skilled in the art that orthogonal radial movement of the jaws is neither necessary nor required. As shown in FIG. 10, in a non-limiting embodiment, the jaw arms 156 may pivot about pivot point P and as such, may result in the radial movement of the jaws being oblique (i.e., in a radial oblique direction) to the axial direction X.

It is also noted that the cinch control arrangement of the present invention is not limited to a medical clip applier device. Rather, it should be understood by those skilled in the art that the above-described cinch control arrangement of present invention may be used in other clip-applying devices, and may also be used in other devices where a cinch is moved axially to widen and/or narrow a gap between a pair of jaws or other members. As described above, the clip applying device 50 of the present invention is able to accept at least two different types of clip cartridges 68a, 68b, and as such, the present invention also provides a cartridge alignment device 36 (shown in FIGS. 23-26) that can center (along central axis CX) clip cartridges 68a, 68b within the elongated tube 60 in a width, or radial direction Z of the cartridges. In other words, the alignment device 36 can maintain the loaded cartridges 68a and 68b in a central position in relation to the sides (i.e., equidistant to the sidewalls of the tube 60 in the radial orthogonal Z axis direction) of the elongated tube 60 (i.e., so that a sagittal plane defined by the X-Y axis bisecting the cartridges 68a, 68b is substantially coplanar with a sagittal plane X-Y that bisects the elongated tube). With such an arrangement, the clip cartridge 68a, 68b can be centered within the elongated tube and the clip cartridge 68a, 68b and the elongated tube, are aligned in the axial direction X (i.e., along the central axis CX). Thus, a clip 52a, 52b can be accurately loaded in the jaws 56 and accurately crimped thereby.

The alignment device 36 has a pair of elongated rails 38 extending in the axial direction X. The rails 38 each have a distal (first) region 38a defining a first channel Ca therebetween, a middle (second) region 38b defining a second channel Cb therebetween, and a proximal (third) region 38c defining a third channel Cc therebetween. Each channel Ca, Cb and Cc successively extends in communication and in the axial direction X. In a non-limiting embodiment, the distal channel Ca is narrower than the middle channel Cb, which in turn is narrower than the proximal channel Cc. The alignment device also has a pair of transition areas 38t (each located between a respective distal region 38a and middle region 38b) which may be tapered or angled to accurately guide the insertion of cartridge 68a into the distal channel Ca, where the cartridge 68a is securely held and centrally aligned therein in the radial direction Z (i.e., cartridge 68a is sandwiched between both distal regions 38a), due to the extending of the distal channel Ca in the axial direction X. In situations where the cartridge 68b is wider in radial direction Z than the cartridge 68a, the cartridge 68b cannot fit within the distal channel 68a. Rather, the transition area blocks the cartridge 68b from being inserted (in the axial direction X) in the distal channel 68a, and also prevents damage to the cartridge 68b during the insertion process. Thus, the cartridge 68b is securely held and centrally aligned in the channel Cb in the radial direction Z (i.e., the cartridge 68b is sandwiched between both middle regions 38b), due to the extension of the middle channel Cb in the axial direction X.

The proximal channel Cc is configured to hold the elongated channel member 58 (through which the cartridge 68a, 68b is inserted), which is inserted therein during the manufacturing/assembly process. Thus, the elongated channel member 58 is also securely held and centrally aligned in the proximal channel Cc in the radial direction Z (i.e., the elongated channel member 58 is sandwiched between both proximal regions 38c), due to the extension of the middle channel Cb in the axial direction X. Additionally, the alignment device 36 also includes a stop region 36s which prevents distal displacement in the axial direction X of the elongated channel member 58. The thickness of a lower portion of the elongated channel member 58 is preferably the same thickness as the lower portion of the stop region, thereby ensuring smooth loading of the cartridges 68a, 68b into their respective channels Ca, Cb.

The alignment device 36 may further include an axially-extending cavity 40 configured to accept the insertion and retraction of the clip-engaging feeder 90 when it loads a clip 52a, 52b (i.e., the cavity 40 can accommodate the feeder 90 therein, between the rails 38), and may further include a ramp portion 42 configured to facilitate the sliding and loading of a clip 52a, 52b into guide slots 194 of the jaws 56. The alignment device may also include a middle inclined region 84, located distally of the cavity 40 and extending in the axial direction X, to assist in the upward distal sliding in the axial direction X of the feeder 90. Further, the alignment device 36 may have an angled or tapered surface 44 at the distal end thereof and/or a semi-cylindrical outer surface 48, to facilitate the insertion of the alignment device, and therefore the clip-applying device 50, into the body cavity.

Figure 37:
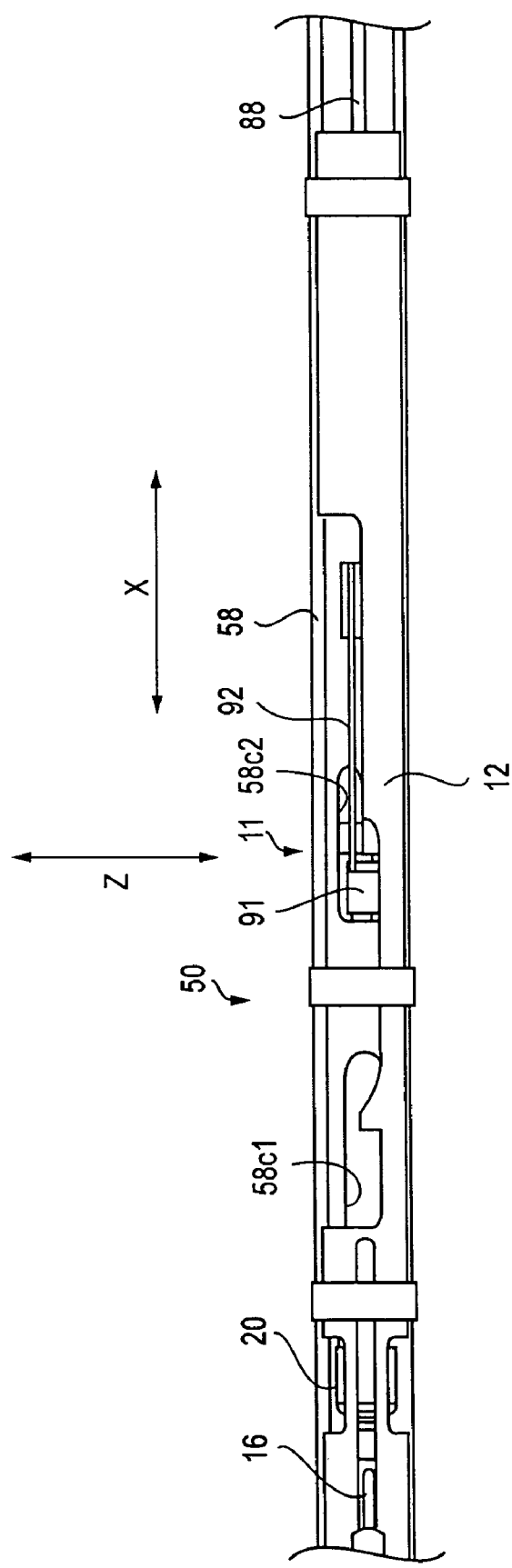
FIG. 37 is a bottom plan view of the slider attached to an underside of a spine and in a distally-moved position.

An advancement block (also referred to as a slider) 12 (shown in FIGS. 27 and 29-36) is attached between the pusher rod 88 and clip-engaging feeder 90 (shown in FIGS. 2-3 and 37). The feeder 90 is movable in axial direction X in relation to the clip-loaded cartridge 68a, 68b disposed within the elongated channel 58; however, the pusher rod is disposed below the elongated channel 58 (shown in FIGS. 6 and 28). The slider 12 has a ladder-engaging toggle 14, which is configured to sequentially engage a series of openings in ladder member 33a, 33b (respectively shown in FIGS. 4-5) slidably arranged within a respective clip cartridge 68a, 68b. The ladder member 33a, 33b, which is engaged by the toggle 14 of the slider 12 (the slider being operatively connected to pusher rod 88 as shown in FIG. 37) is pushed in the distal direction (along axial direction X) to in turn push against the proximal-most or last clip 52a", 52b" in the cartridge 68a, 68b, so as to also push distally the next adjacent clip(s) 52a, 52b within that cartridge 68a, 68b. Forward (or distal) advance of the series of clips 52a, 52b loaded within the cartridge 68 is thus effected.

As shown in FIGS. 27 and 29-36, the ladder-engaging toggle 14 pivots in both directions about a pivot shaft 20, at least a portion of the pivot shaft generally extending in the orthogonal radial direction Z (i.e., generally orthogonal to the axial direction X). Thus, the toggle is pivotable about the Z axis. As best shown in FIGS. 33-36, the pivot shaft 30 may be generally shaped like a U or J, so that the pivot shaft does not slide out of the slider 12. Alternatively, the pivot shaft may have elongated shaft ends, rivets and the like to prevent such sliding out of the slider 12.

Figure 28:
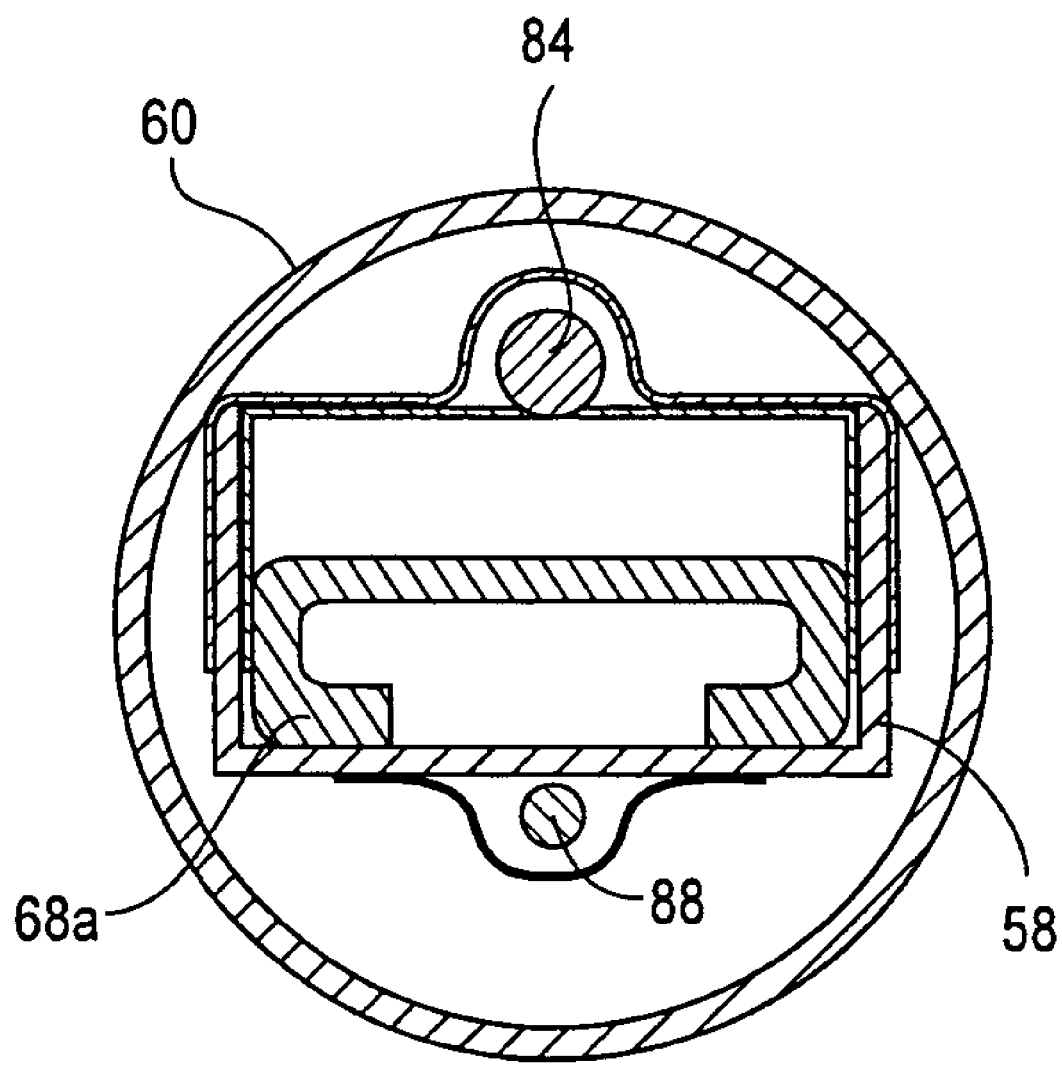
FIG. 28 is a front cross-sectional view of the elongated tube taken along the lines of 28-28 in FIG. 6.
Figure 29:
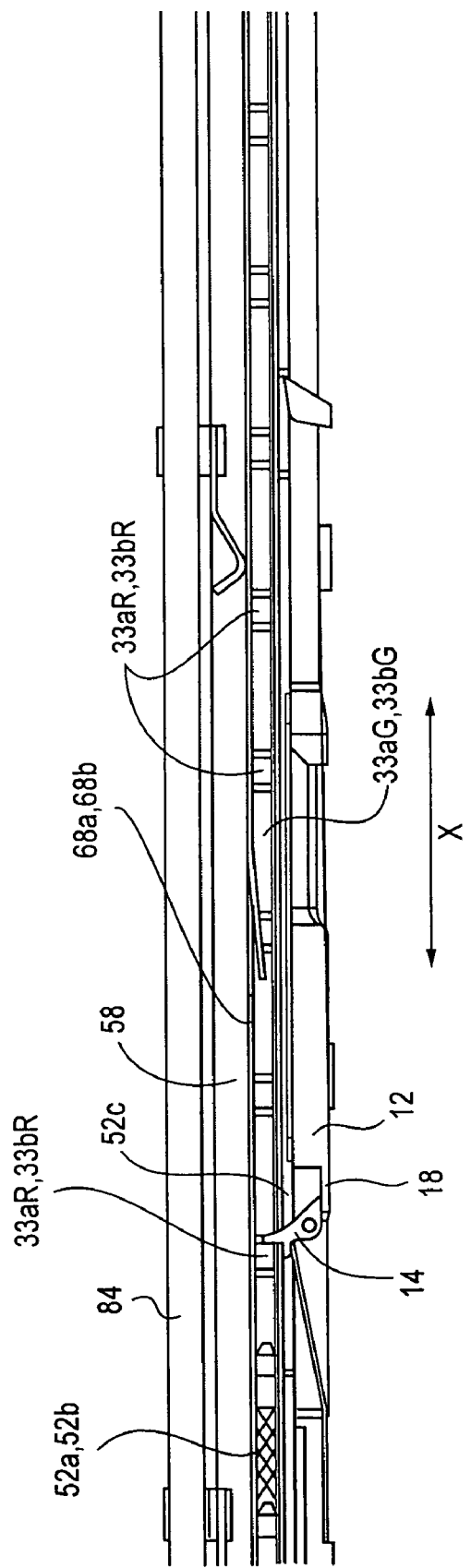
FIG. 29 is a sectional view of a slider toggle in an upright position.
Figure 30:
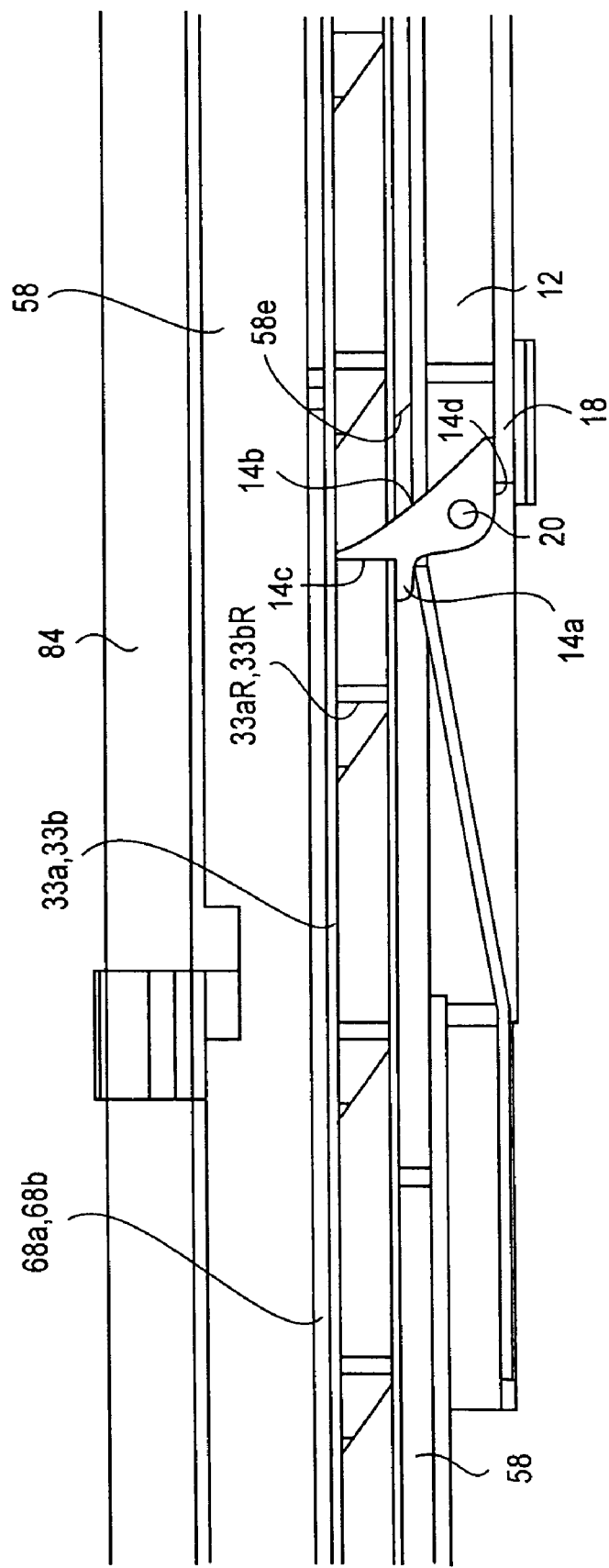
FIG. 30 is an enlarged sectional view of the slider toggle shown in FIG. 29.
Figure 31:
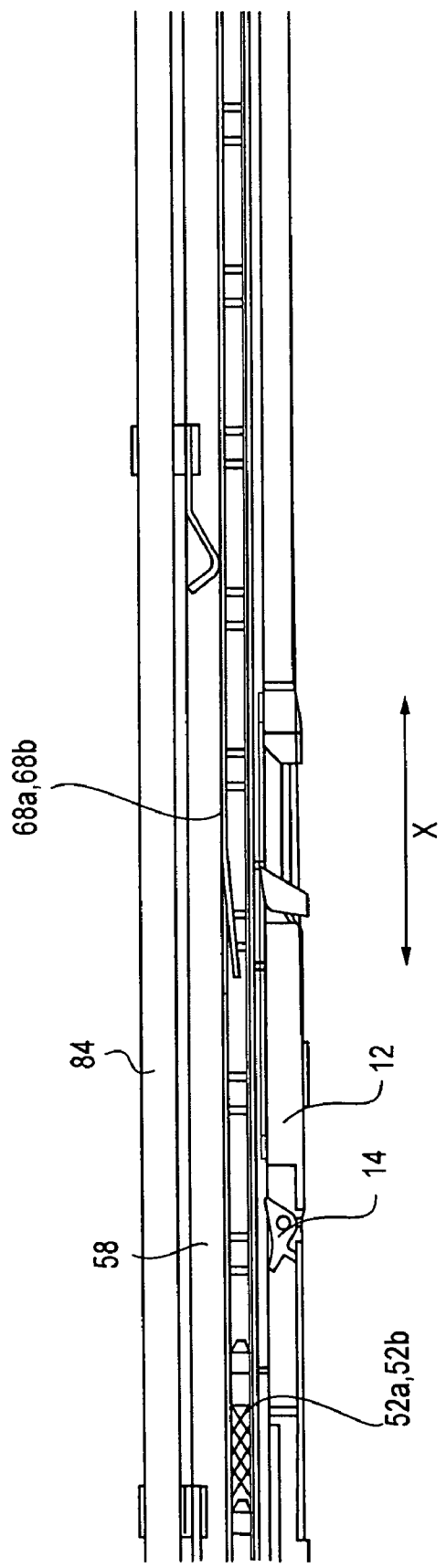
FIG. 31 is a sectional view of the slider toggle in a lowered position.
Figure 32:
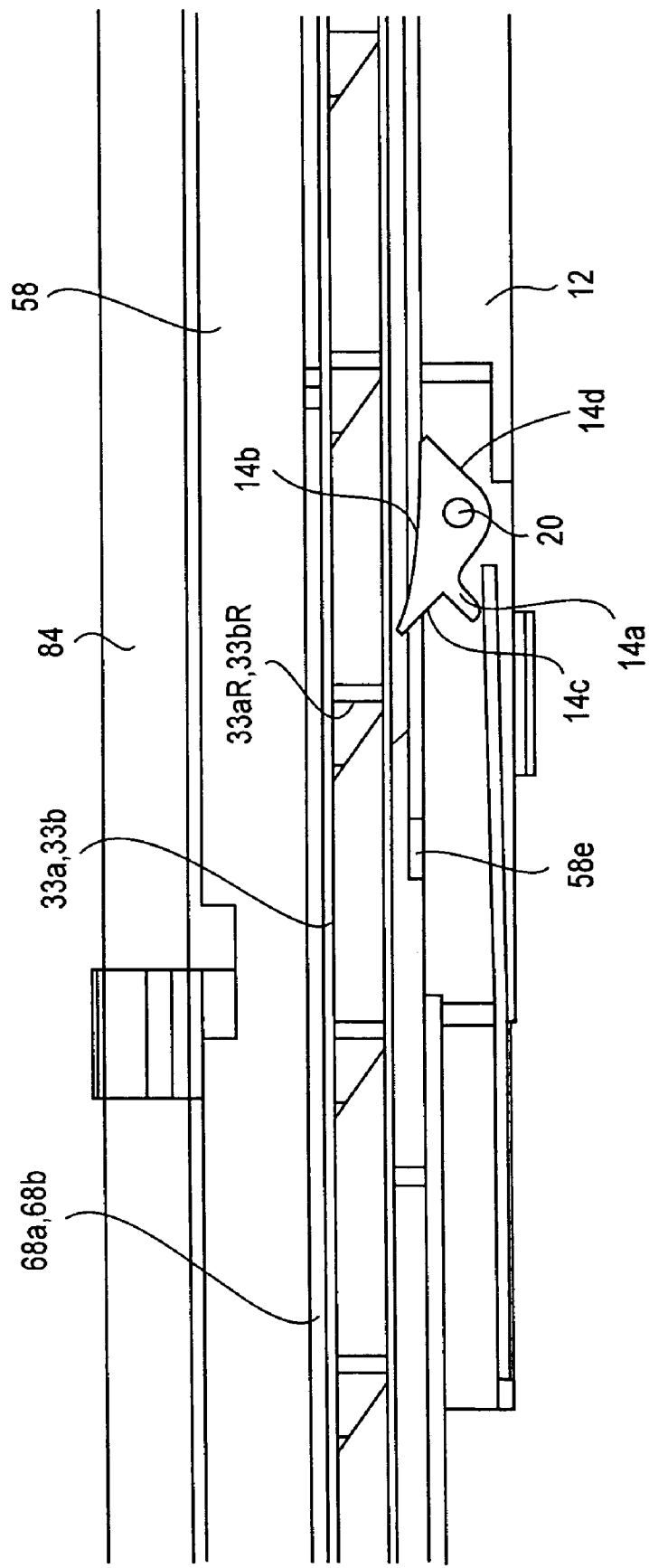
FIG. 32 is an enlarged sectional view of the slider shown in FIG. 31.
Figure 33:
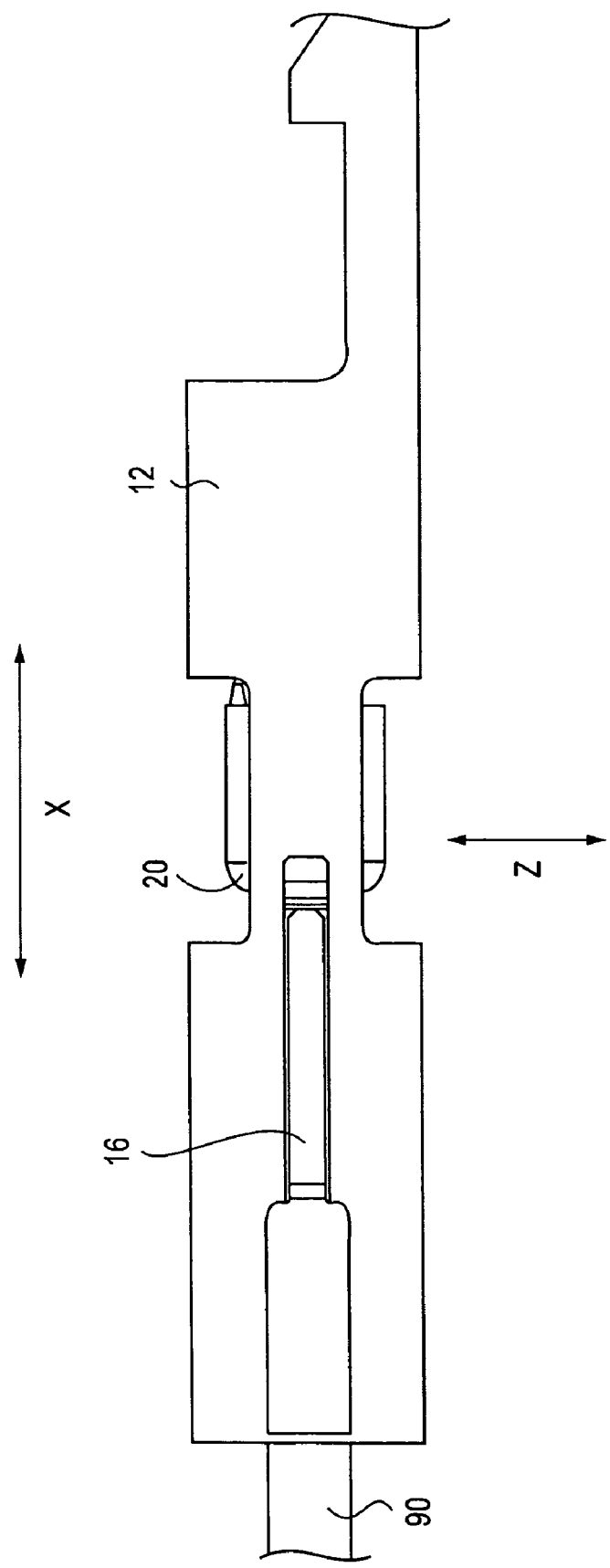
FIG. 33 is a bottom plan view of the slider.
Figure 34:
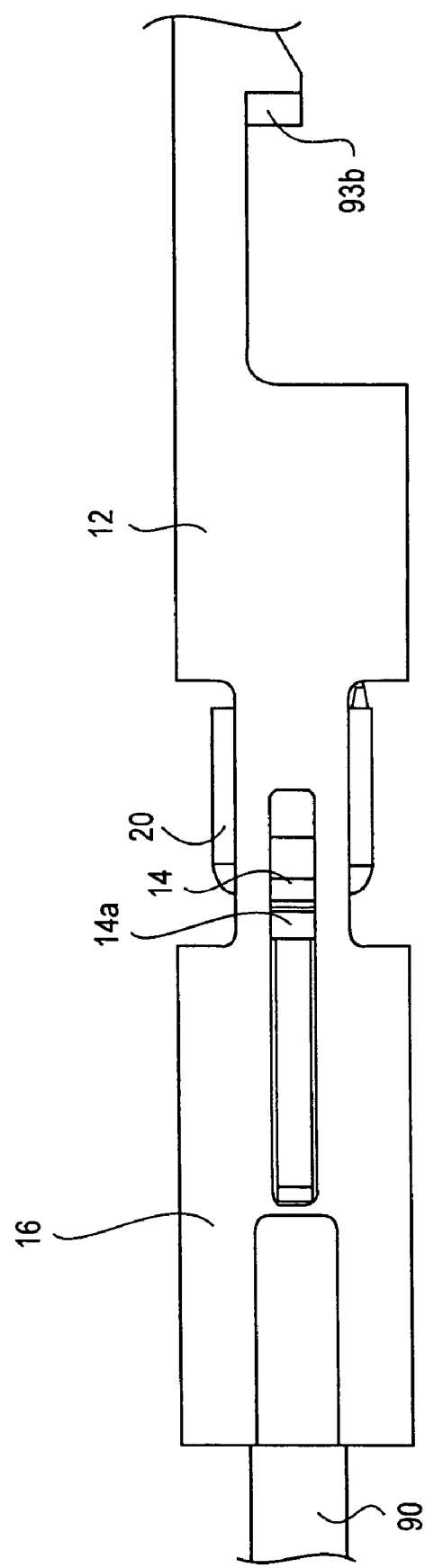
FIG. 34 is a top plan view of the slider.
Figure 35:
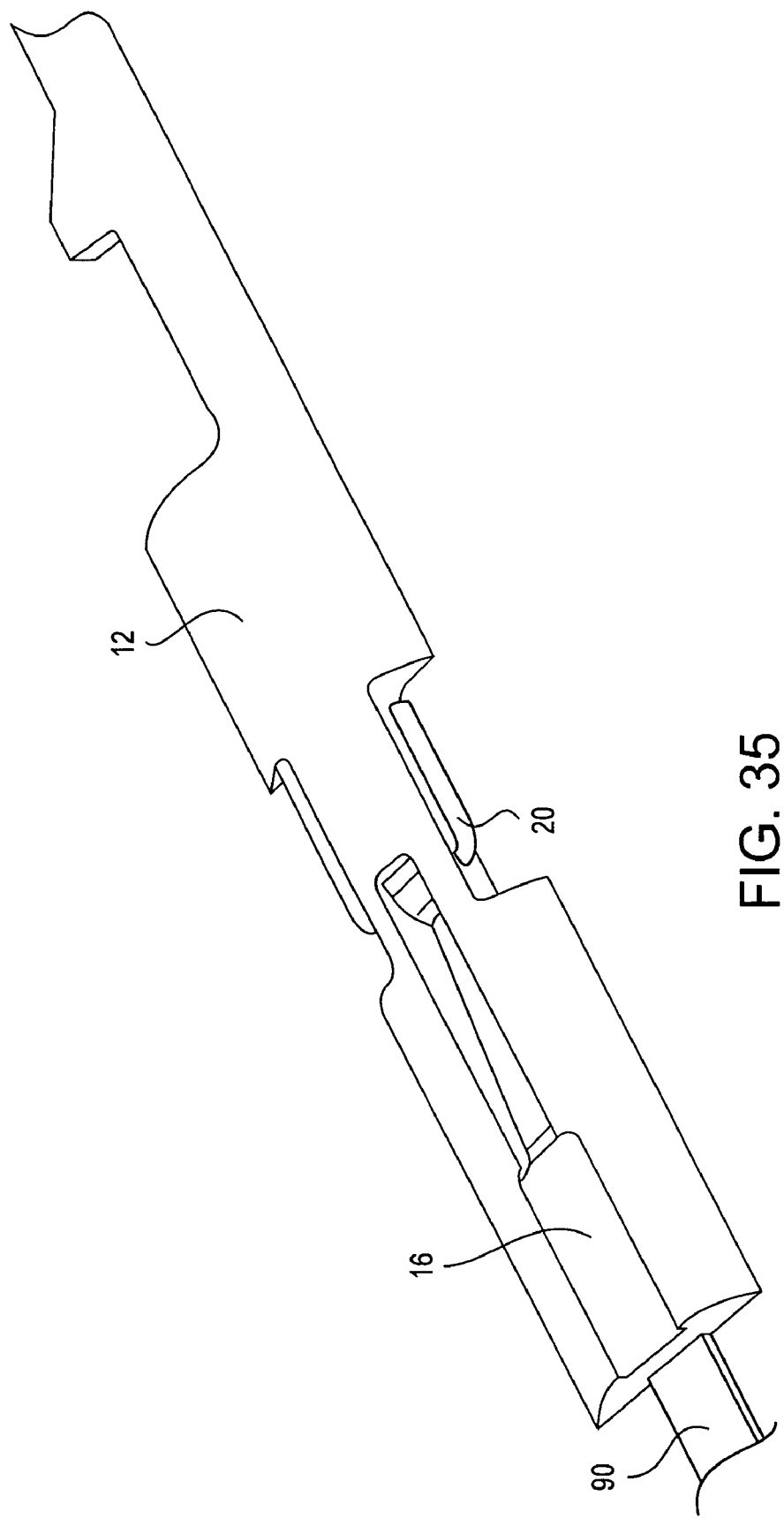
FIG. 35 is a perspective view of the underside of the slider.
Figure 36:
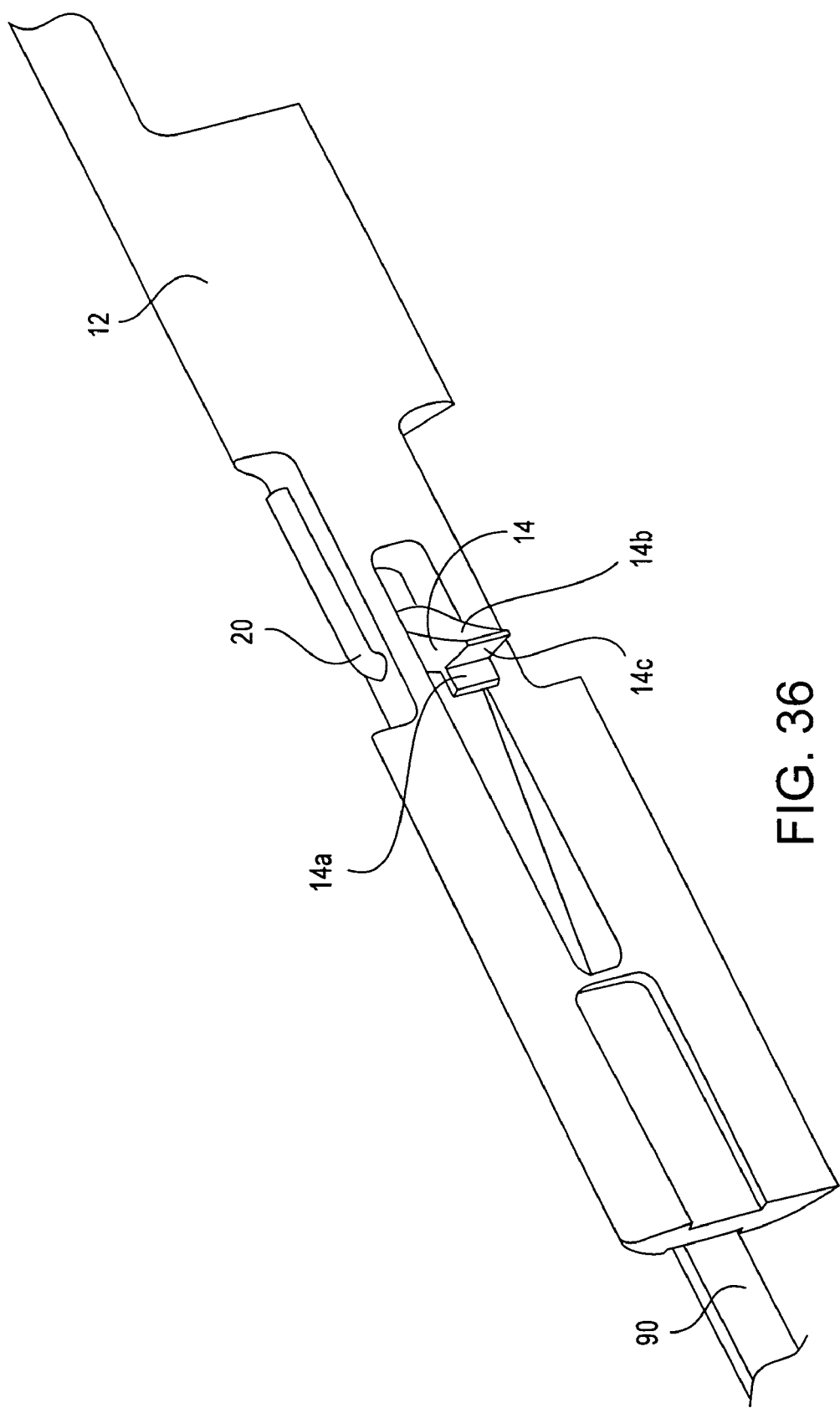
FIG. 36 is a perspective view of the top of the slider.

In a non-limiting embodiment, the toggle 14 is generally shaped like a right triangle, but it should be readily appreciable by those skilled in the art that the toggle can take any variety of desirable shapes and configurations. The toggle 14 has a ridge 14a that engages a toggle spring 16 affixed to the slider 12. The spring 16 may be a leaf spring (but can be other biasing devices including but not limited to a coil spring or other spring-like members formed, e.g., of an elastomeric material), which engages the ridge 14a to bias the toggle in an upright (second) position, shown in FIGS. 30-31 and 36. In a non-limiting embodiment and as shown in FIG. 28, the channel is generally U-shaped, and as described above, the slider 12 proximally and distally slides below and adjacent to the channel 58 in the axial direction X. The channel 58 additionally includes a toggle aperture 58C1 in the bottom portion thereof, through which a portion of the toggle 14 is inserted, when the toggle is in the upright position.

Operation of the clip advancement arrangement according to an embodiment of the present invention will now be described. When the trigger 64 is squeezed, the slider 12 is moved proximally in the axial direction X (since the slider is operably connected to the pusher rod 88, which is in turn connected to the proximal bearing 76). As the slider 12 is moved proximally, an edge-engaging face 14b of the toggle 14 engages an edge 58e of the channel 58, such that the channel edge 58e (which generally extends in the Z axis direction) pushes the toggle 14 to rotate in a first direction (e.g., counterclockwise when viewing FIGS. 31-32) to a lowered (first) position and against the biasing force of the toggle spring 16, shown in FIGS. 31-32. In the first position, the toggle 14 slides in the axial direction X and below the channel 58, with at least a portion of the edge-engaging face 14b contacting the underside of the channel 58. It is noted that the channel edge 58e may be angled or tapered to increase the surface area thereof, thereby ensuring smooth and precise pivoting action of the toggle 14.

When the trigger 64 is released, the slider 12 begins to distally move in the axial direction X. The edge-engaging face 14b contacts the underside of the channel 58 until the toggle 14 reaches the toggle aperture 58C1, at which point the edge-engaging face 14b contacts the channel edge 58e and allows the toggle spring 16 to urge the toggle into the upright position (shown in FIGS. 30-31 and 36) and between rungs 33aR, 33bR of the ladder member 33a, 33b, the rungs having rung gaps 33aG, 33bG therebetween. Thus, the toggle 14 rotates in a second direction (clockwise when viewing FIGS. 29-30). Pivoting of the toggle 14 in the second direction is stopped when a heel portion 14d engages a stop portion 18 located on the slider 12.

Once in the upright position, the toggle 14 continues to move distally through the toggle aperture 58C1 (and within a rung gap 33aG, 33bG) in the axial direction X such that a pushing face 14c contacts a rear (proximal) side of a rung 33aR, 33bR of the ladder member 33a, 33b. Thus, the toggle 14 pushes the ladder member 33a, 33b in the distal direction (along axial direction X) to in turn push against the proximal-most or last clip 52a", 52b" in the cartridge 68a, 68b to also push distally the next adjacent clip(s) 52a, 52b. It is noted that while the rungs 33aR, 33bR of the figures extend in the Z axis direction, those skilled in the art will readily appreciate that the rungs could be differently configured in alternative embodiments, including but not limited to, e.g., angled and arcuate.

The above process may be repeated by continually squeezing and releasing the trigger 64, which in turn continually distally advances the ladder member 33a, 33b to distally push clips 52a and 52b, until the last clip 52a", 52b" is loaded into and applied by the jaws 56.

It is noted that while many of the figures show the clip advancement arrangement of the present invention being used in a clip applying device 50 that can accept more than one type of clip supply cartridge 68a, 68b, it should be readily understood by those skilled in the art that the clip advancement arrangement of present invention may be used in a clip applying device that can accept only a single type of cartridge, or alternatively, may be used in a clip applying device having clips pre-installed therein.

FIG. 37 shows a trigger lockout arrangement 11. As described above, the slider 12 is attached between the pusher rod 88 and clip-engaging feeder 90. The trigger lockout arrangement 11 serves to lock movement of the trigger 64 when the last clip 52a", 52b" of the cartridge 68a, 68b has been applied by the jaws 56, thereby reducing the likelihood of tissue damage by squeezing jaws without a staple therein, and alerting the surgeon that additional clips are required.

Also as discussed above, when the trigger 64 is squeezed, the slider 12 proximally moves in the axial direction X, and when the trigger is released, the slider moves in the axial direction X such that the toggle 14 distally advances the ladder member 33a, 33b by one clip and such that the feeder 90 loads the distalmost clip 52a', 52b' between the jaws 56.

The channel member 58 also includes a block 91 affixed to the underside of the channel member via a flexible rod 92, and additionally has a block aperture 58C2, located above the block 91 in the Y-axis direction, for accepting insertion of at least a portion of the block 91 therein. At rest, the flexible rod 92 is biased to generally extend in the axial direction X. The slider 12 also has a tooth 93 that contacts the block 91 when the slider is proximally or distally moved in the axial direction X. While the block 91 is shown as being cubical in arrangement, it should be understood by those skilled in the art that in alternative embodiments the block can take a variety of shapes, including but not limited to, e.g., a trapezoid, frustum or ovoid.

Figure 38:
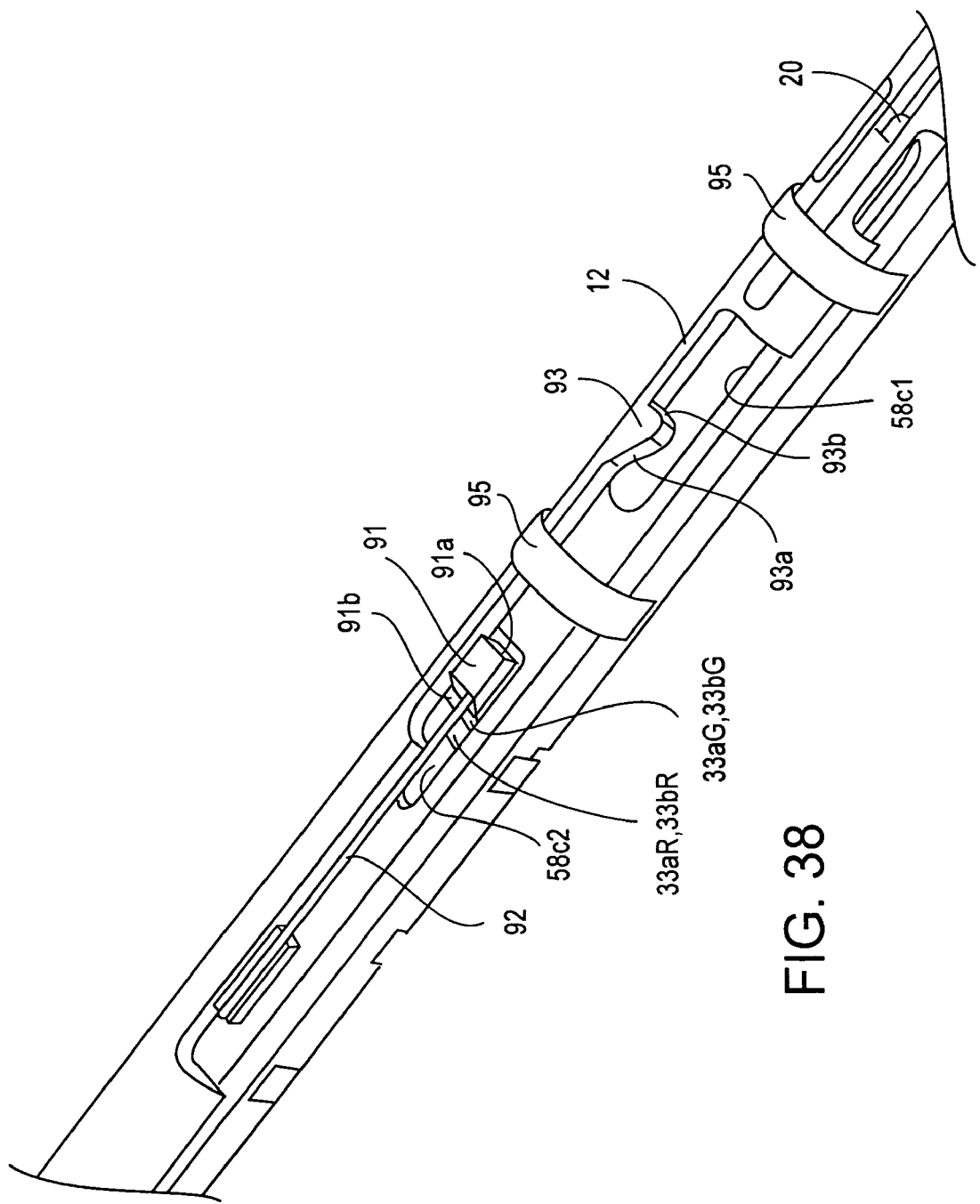
FIG. 38 is a bottom perspective view of the slider attached to an underside of a spine and in a distally-moved position.

Specifically, as shown in FIG. 38, when the trigger 64 is squeezed and the slider 12 moves proximally in the axial direction X (to approach the block 91 from the front, shown in FIGS. 37-38), a rear surface 93a of the tooth 93 engages a front surface 91a of the block 91 to move the block in radial direction Z while the slider continues to move proximally. The rear surface 93a of the tooth 93 is angled to facilitate movement of the block 91 in the radial direction Z. Once the slider 12 passes the block 91, the block returns to its original rest position due to the biasing action of the rod 92.

Figure 39:
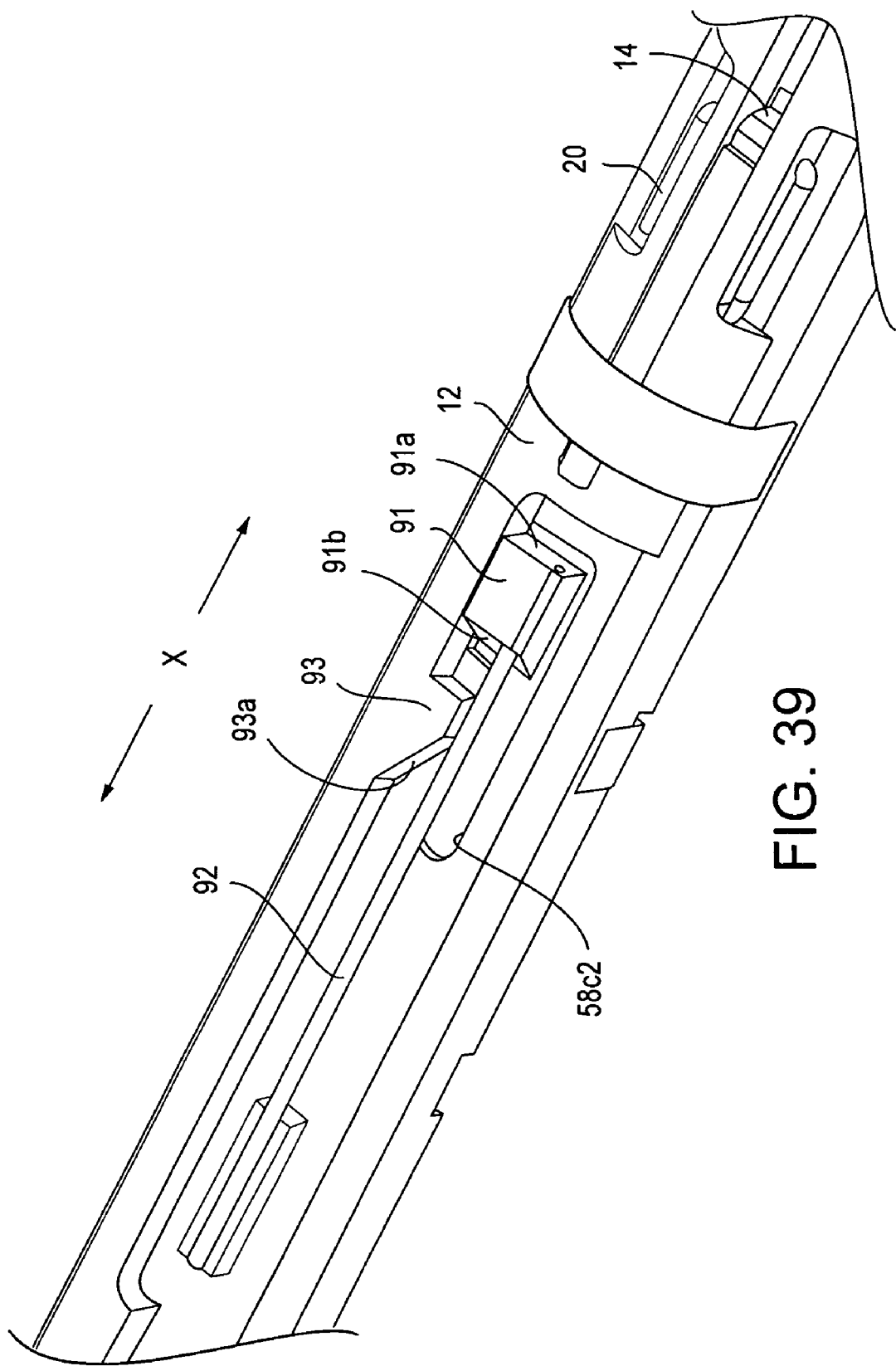
FIG. 39 is a bottom perspective view of the slider attached to an underside of a spine and in a proximally-moved position.

When the trigger 64 is released, the slider 12 begins to move distally in the axial direction X and approaches the block 91 from the rear (shown in FIG. 39). If a cartridge 68a, 68b having a plurality of clips 52a, 52b has been loaded into the clip applier 50, the slider moves distally such that a front surface 93b (best shown in FIG. 38) of the tooth 93 engages a rear surface 91b of the block 91 to push the block upward in the Y-axis direction (i.e., into the page of FIG. 37). Specifically, the upward movement of the block 91 causes a portion of the block to pass through the block aperture 58C2 of the channel 58 and be inserted between the rungs 33aR, 33bR of the ladder member 33a, 33b (i.e., the portion of the block is inserted into a rung gap 33aG, 33bG), thereby creating clearance for the tooth 93 to pass over the block 91 as the slider continues to move in the distal direction. Once the tooth 93 has passed over the block 91, the rod 92 urges the block downwardly, since the rod 92 is biased in the axial direction X and to keep the block out of the ladder gap 33aG, 33bG.

To facilitate precise movement of the block 91 in the Y-axis direction, the front surface 93b of the tooth 93 and/or the rear surface 91b of the block 91 may be angled. Additionally, one or more bands 95 to slidably secure the slider 12 against the underside of the channel 58 may be provided, thereby securing the slider against movement in the Y-axis direction, when the slider moves in the axial direction X. The presence of the block 91 between the rungs 33aR, 33bR of the ladder member 33a, 33b does not interfere with the distal movement of the ladder member by the toggle, since these two operations are out of phase, i.e., during distal movement of the slider 12, the toggle 14 does not engage a rung 33aR, 33bR until after the tooth 93 has passed over the block 91 and the block has withdrawn from the ladder gap 33aG, 33bG.

As described above, the slider may be continually moved proximally and distally by respective continual squeezing and releasing of the trigger 64, until the last clip 52a", 52b" is loaded into and applied by the jaws 56. While the last clip 52a", 52b" is being loaded into the jaws 56 by the feeder 90 (and thus no more clips 52a, 52b are serially loaded within the cartridge 68a, 68b), the toggle 14 engages the rung 33aR, 33bR, thereby advancing the ladder member 33a, 33b a final time and exposing a solid surface 96 of the ladder member beneath the block aperture 58C2 (i.e., there is no longer a ladder gap 33aG, 33bG beneath the block 91). The clip applying device 50 is now ready for one final clip crimping process. During the final clip crimping process, the trigger 64 is squeezed to proximally move the slider 12 (and to thereby bring the tooth 91 thereof behind the block, as described above) and to distally move the cinch 86 to crimp the last clip 52a", 52b".

Figure 40:
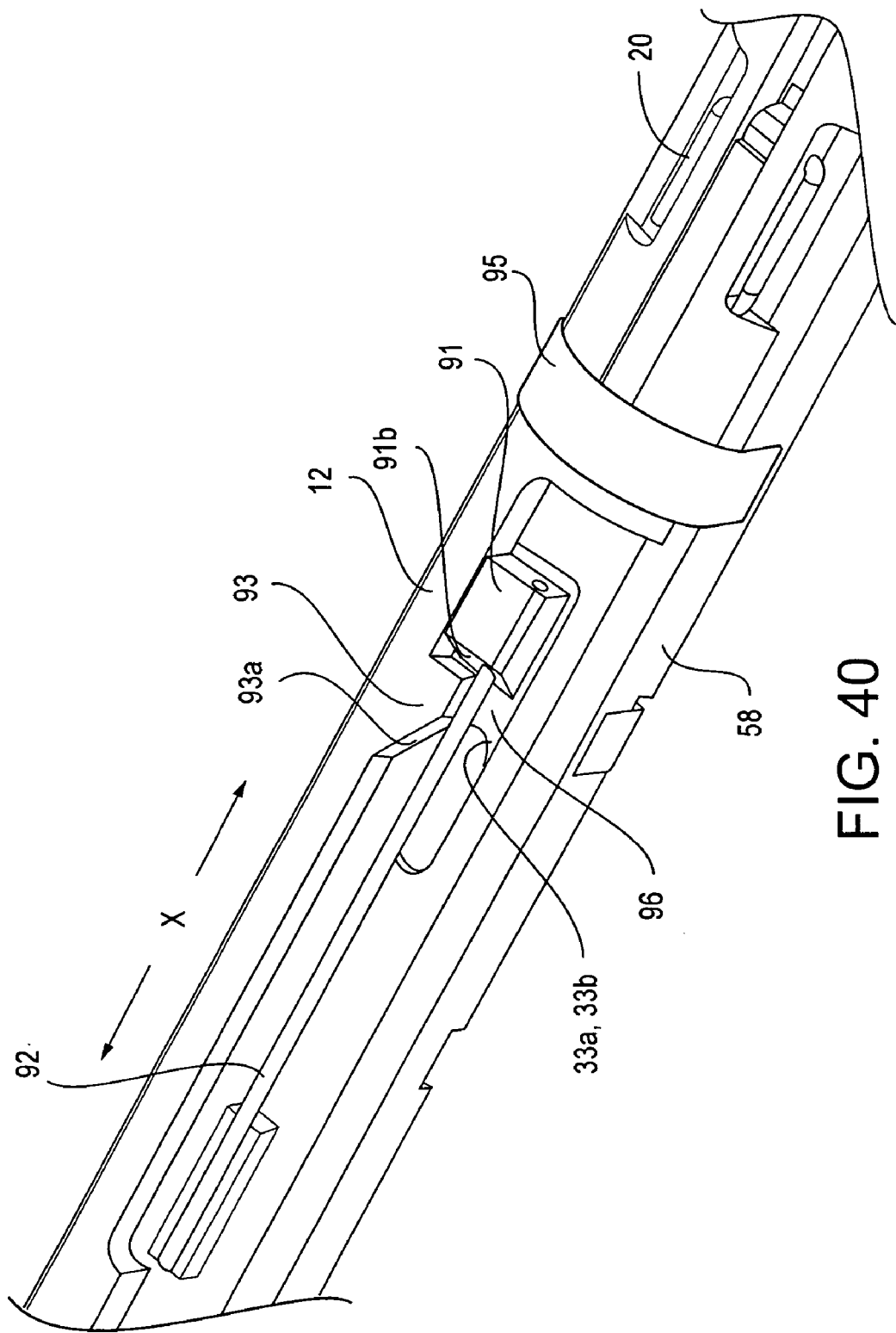
FIG. 40 is a bottom perspective view of the slider attached to an underside of a spine and in a proximally-moved and locked position.

As shown in FIG. 40, when the trigger 64 is released after the last clip 52a", 52b" has been crimped, the compression spring 78 urges the trigger toward the open position, which (as described above) moves the slider 12 distally so that the tooth 93 engages the block 91. However, the solid surface 96 of the ladder member 33a, 33b prevents displacement of the block 91 by the tooth 93 in the Y-axis direction (since there is no ladder gap 33aG, 33bG for the block to enter. Thus, the tooth 93 abuts against the block and is prevented from distally moving in the axial direction X, thereby locking the trigger in the closed position and alerting the surgeon that the last clip 52a", 52b" has been applied. As noted above, the bands 95 prevent the slider (and thereby the tooth 93) from being displaced in the Y-axis direction so that the tooth does not "leap over" the block 91, when the slider moves in the axial direction X. It is noted, however, that the trigger 64 is permitted to be slightly unsqueezed so that the last clip 52a", 52b" and any tissue can be released from the jaws 56. Once the cartridge 68a, 68b has been removed from the clip applying device 50, the trigger 64 is free to again move to the unsqueezed position, since the solid surface 96 is no longer present.

An embodiment of the present invention uses cartridges 68a, 68b having twenty clips 52a, 52b, however, it should be understood by those skilled in the art that the present invention may use cartridges having fewer or greater than twenty clips. Additionally, while an embodiment of the trigger lockout arrangement 11 of the present invention locks the trigger 64 after all of the clips 52a, 52b have been applied, it should be understood by those skilled in the art that the trigger lockout arrangement may lock the trigger when one or more clips 52a, 52b remains in the cartridge 68a, 68b or the clip applying device 50.

It is noted that while many of the figures show the trigger lockout arrangement of the present invention being used in a clip applying device 50 that can accept more than one type of clip supply cartridge 68a, 68b, it should be readily understood by those skilled in the art that the trigger lockout arrangement of present invention may be used in a clip applying device that can accept only a single type of cartridge, or alternatively, may be used in a clip applying device having clips pre-installed therein.

Figure 41:
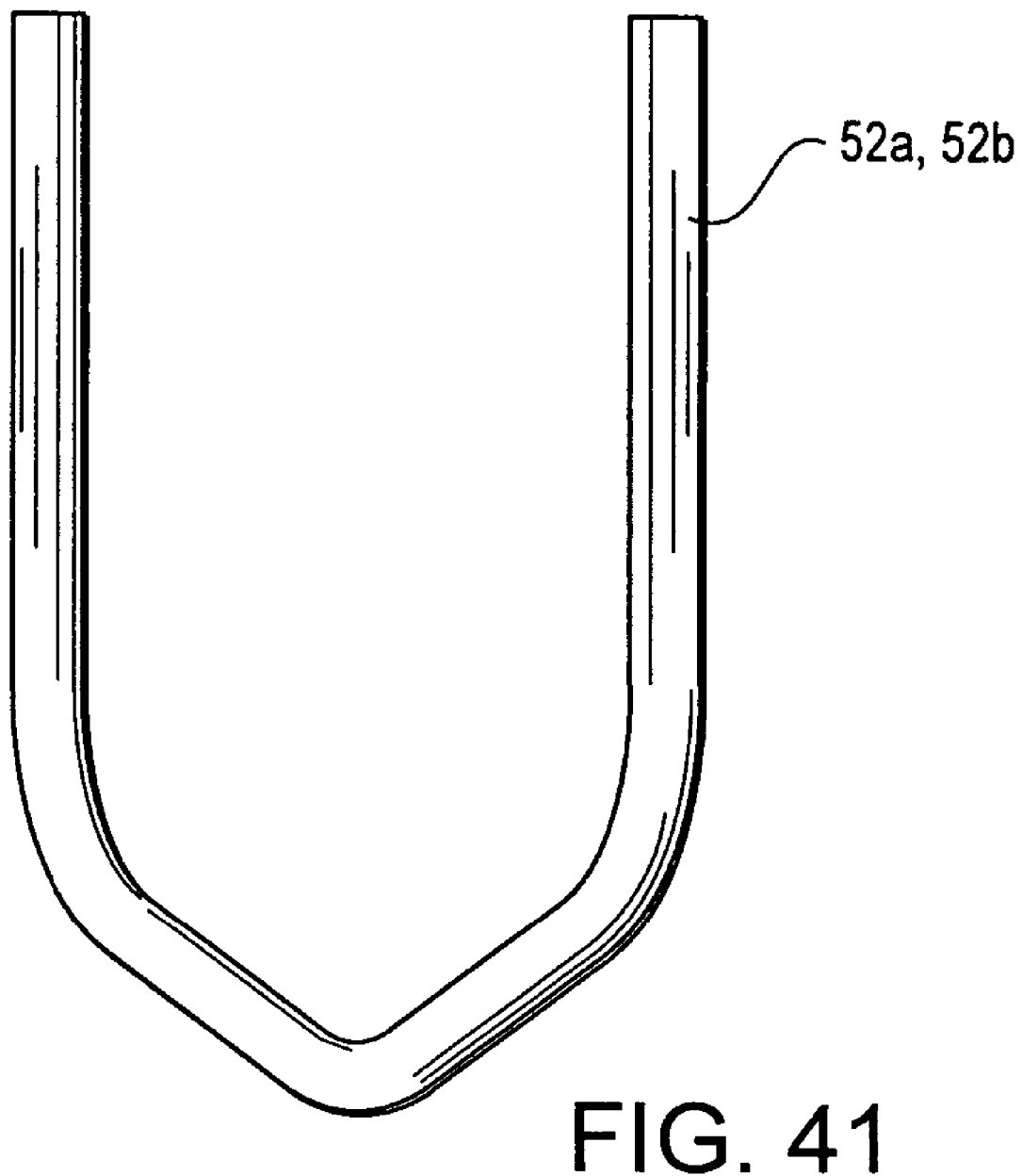
FIG. 41 is a plan view of an uncrimped clip for use in an embodiment of the present invention.
Figure 42:
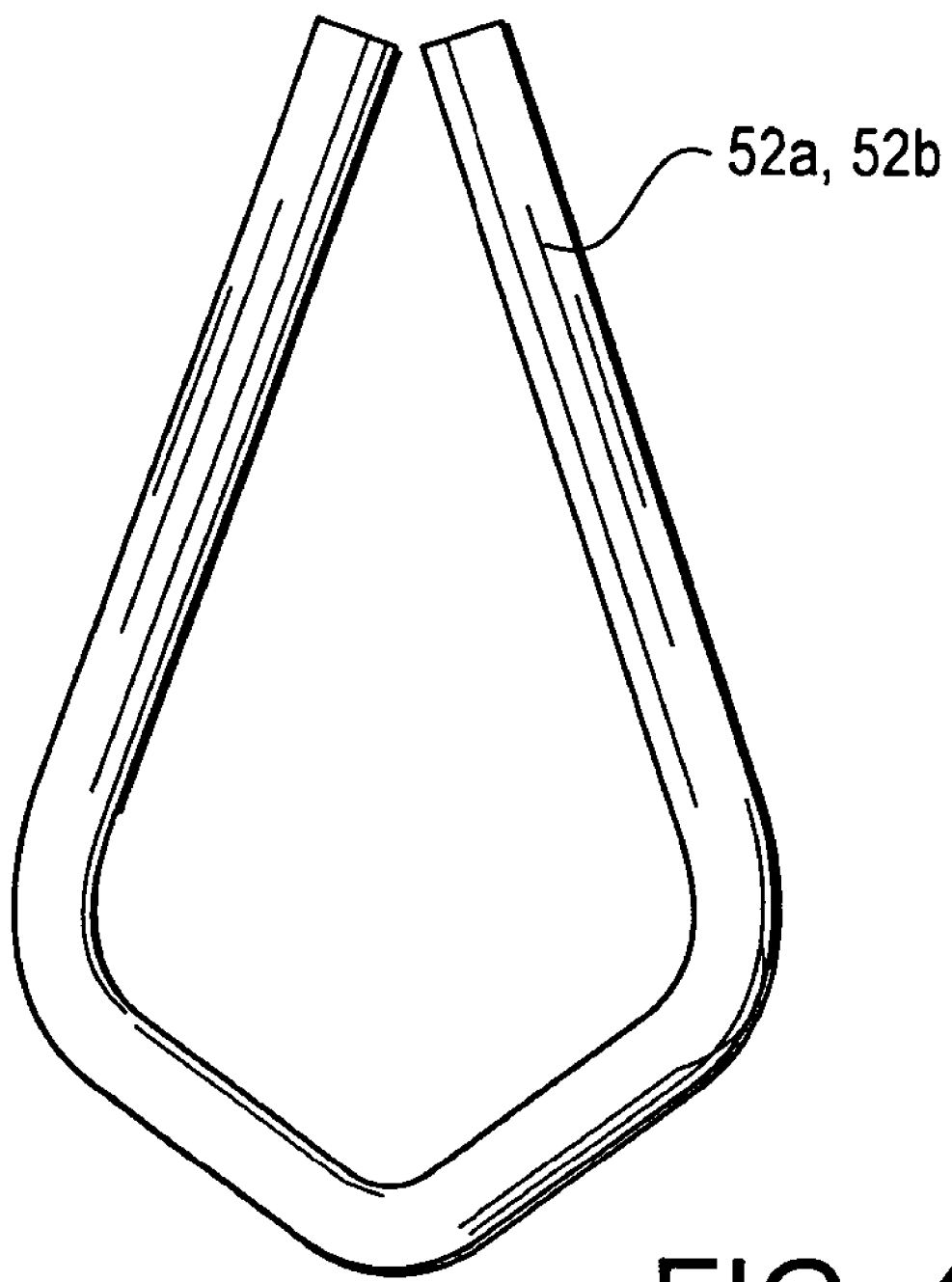
FIG. 42 is a plan view of a partially crimped clip for use in an embodiment of the present invention.
Figure 43:
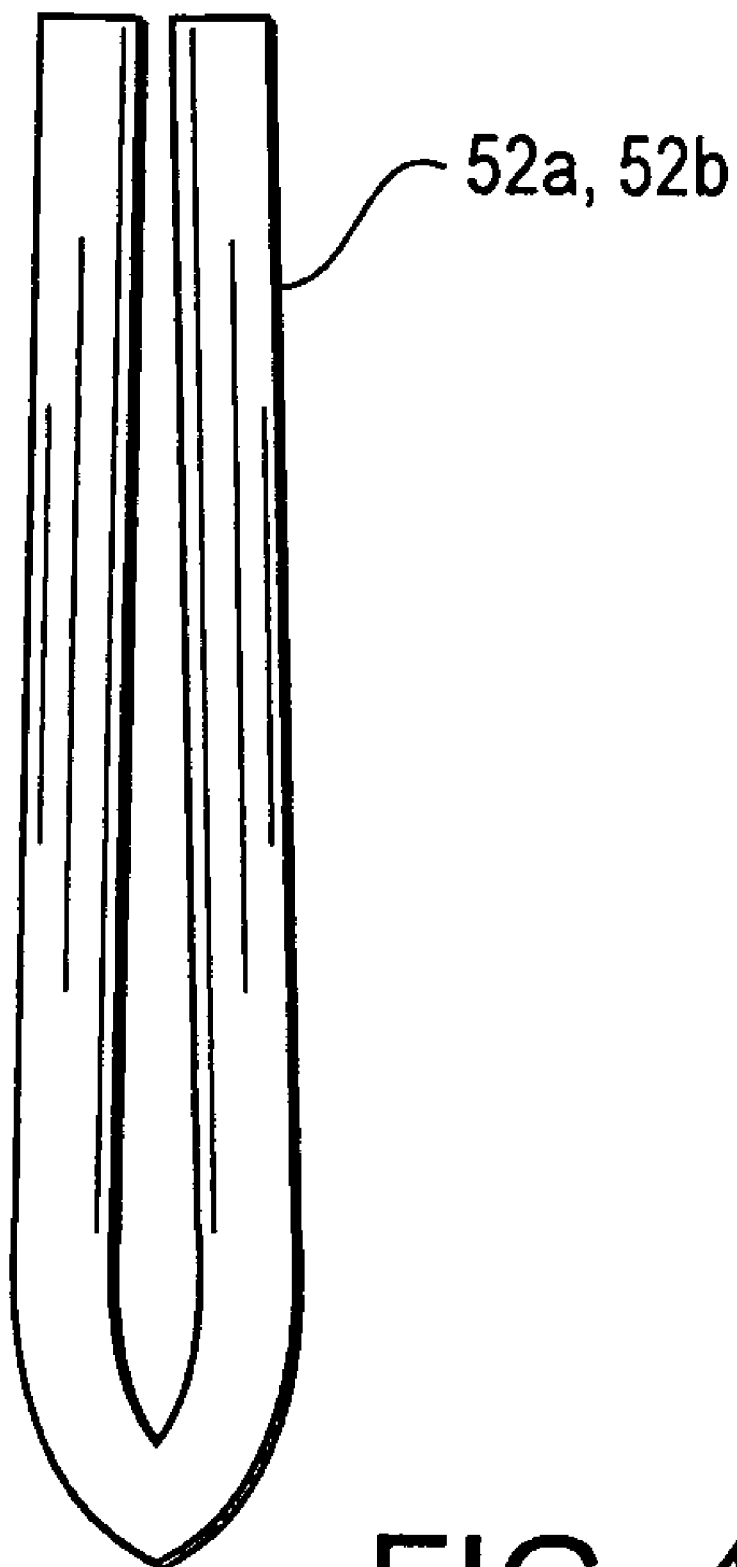
FIG. 43 is a plan view of a generally fully crimped clip for use in an embodiment of the present invention.

Another feature of an embodiment of the present invention includes a system for indicating to the surgeon when the clip 52a, 52b has been partially crimped (shown in FIG. 42) and/or when the clip 52a, 52b has been generally fully crimped (shown in FIG. 43). FIG. 41 shows an uncrimped clip. During surgery, a surgeon may want to apply a clip 52a, 52b, yet still leave a gap between the legs of the clip to allow passage of a blood vessel therethrough, thereby allowing blood to flow through the vessel unobstructed. When a surgeon partially squeezes the trigger 64, the jaws 56 are only partially closed and the clip 52a, 52b may thus be applied in a partially crimped configuration. This partially-squeezed position is referred to as the cholangio zone. It is thus desirable to alert the surgeon (visually, audibly and/or tactilely) as to when the clip applying device 50 is in the cholangio zone (shown in FIGS. 12 and 44). It is further desirable to alert the surgeon (visually, audibly and/or tactilely) as to when the clip applying device is in fully squeezed position (shown in FIG. 45).

The clip applying device 50 may include a visual slider 102 (housed within the handle grip assembly 62) which slides along an indicator path by way of indicator shaft 104 in an inclined direction with respect to the longitudinal axis X, although it should be understood by those skilled in the art that the indicator shaft 104 may be parallel or declined with respect to longitudinal axis X in alternative embodiments. The visual slider is biased in the general distal direction by a shaft spring 106 which may be disposed about the proximal end of the indicator shaft. Alternatively, the shaft spring 106 may be disposed at the distal end of the indicator shaft 104 to "pull" the visual slider toward the distal end of the grip assembly 62.

The visual slider 102 includes three indicator regions 102a, 102b, 102c, each having different indicia for indicating the position of the trigger, for example, the color, pattern or wording on each region may be different. Each region 102a, 102b, 102c is alternatively visible through a window 111 located in the top of the grip assembly. As a non limiting example, indicator region 102a (indicating the open trigger position) may be green, indicator region 102b (indicating the cholangio zone) may be yellow, and indicator region 102c (indicating the generally fully-squeezed position) may be red. Alternatively, each indicator region 102a, 102b, 102c may show, e.g., different wording (e.g., "open," "partial," "closed"), a different symbol, or a different pattern.

In the unsqueezed position (shown in FIG. 1), a first abutment surface 102d of the visual slider 102 abuts against a first end 112a of a pivotable trip switch 112 to maintain the visual slider in its distalmost position (against the distal biasing force of the shaft spring 106), and indicator region 102a is displayed through the window 110. The trip switch 112 has a trip switch spring 114 which is affixed to the grip assembly 62 to bias the trip switch to pivot in the counterclockwise direction (when viewed in FIG. 1). Additionally, a second end 112b of the trip switch 112 engages an outer surface of the distal bearing to prevent further counterclockwise pivoting of the trip switch.

Figure 12:
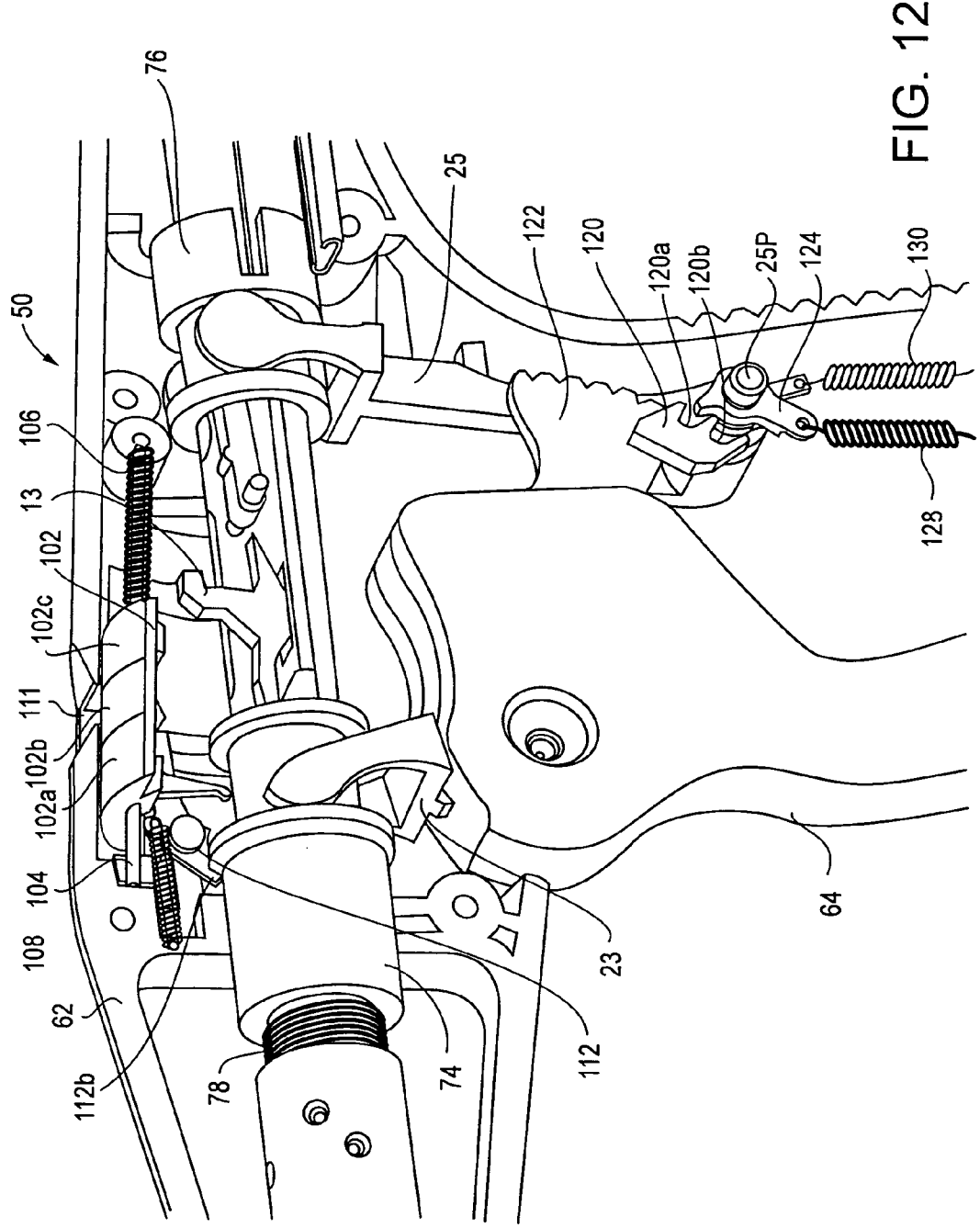
FIG. 12 is an enlarged sectional view of a handle grip assembly of an embodiment of the present invention.
Figure 44:
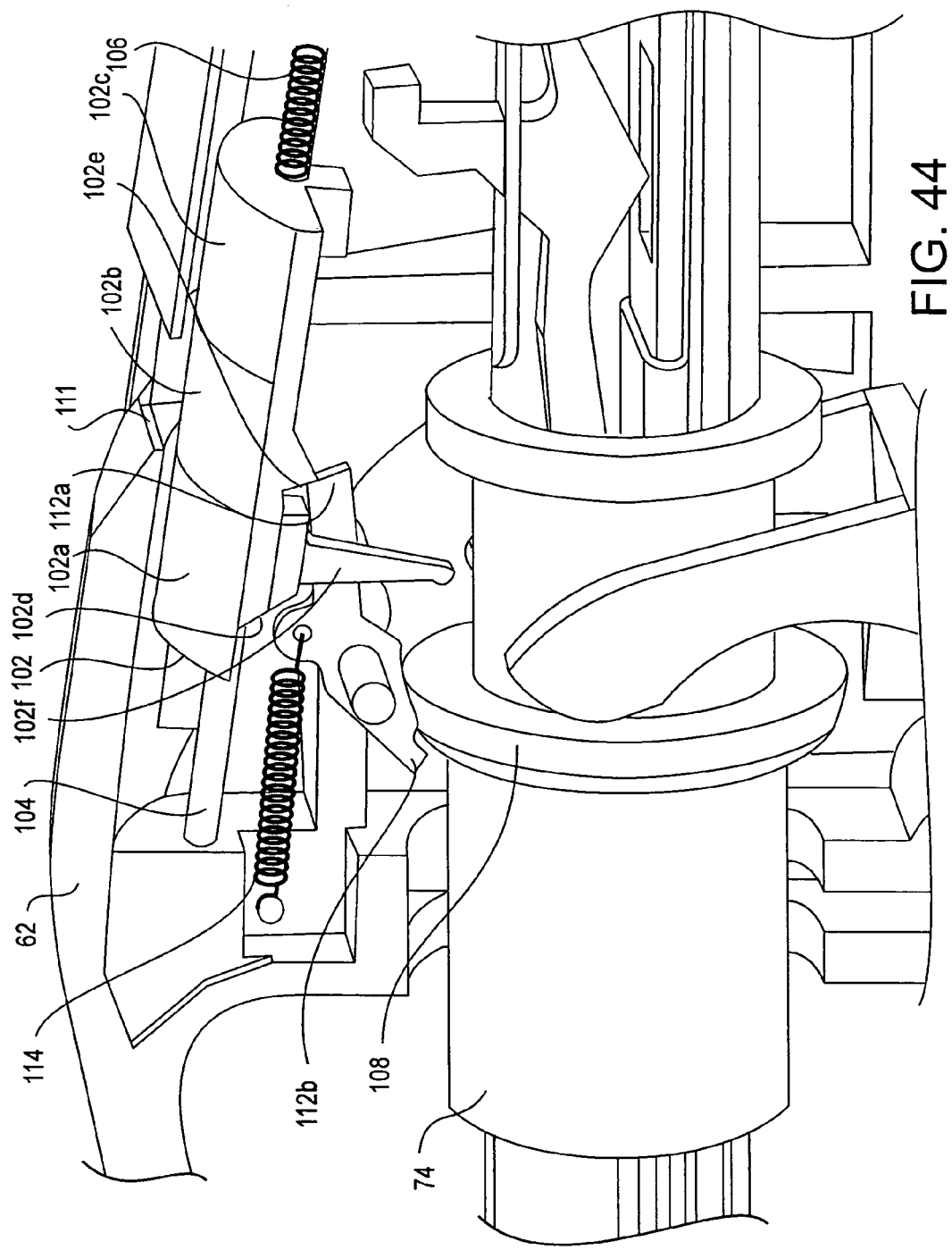
FIG. 44 is an enlarged perspective sectional view of an indicating arrangement according to an embodiment of the present invention in a partially-crimped position.

When the trigger 64 is squeezed toward the cholangio zone (and the distal bearing begins to move distally along axial direction X), the visual slider 102 remains in position (due to the continued engagement of the first abutment surface 102d with the first end 112a of the trip switch 112) until an angled distal surface of a distal bearing ring 108 engages the second end 112b of the trip switch to pivot the trip switch clockwise (when viewed in FIG. 1), which disengages the first abutment surface 102d from the first end 112a of the trip switch 112, thereby allowing the shaft spring 106 to distally urge the visual slider 102. The visual slider is distally urged until the first end 112a of the trip switch 112 engages a second abutment surface 102e of the visual slider 102 to stop distal movement of the visual slider and exposing the indicator region 102b through the window 111 (indicating the cholangio zone to the surgeon), as shown in FIGS. 12 and 44.

When the trigger is squeezed from the cholangio zone to the generally fully squeezed position (and thus the distal bearing continues to move distally to cause the jaws 56 to generally fully crimp the clip 52a, 52b), the outer circumference of the distal bearing ring 108 further engages the second end 112b of the trip switch 112 to further pivot the trip switch clockwise, which disengages the second abutment surface 102d from the first end 112a of the trip switch 112, thereby allowing the shaft spring 106 to further distally urge the visual slider 102 until the slider reaches its limit of distal travel along the indicator shaft 104, thereby exposing the indicator region 102c through the window 111 (indicating the generally fully squeezed position to the surgeon), as shown in FIG. 45.

When the trigger 64 is released (and the distal bearing begins to move proximally due to the biasing force of the compression spring 78), a proximal face of the distal bearing ring 108 engages an indicator finger 102f to proximally move the visual slider 102 so that the first abutment surface 102d of the visual slider 102 again abuts against a first end 112a of the trip switch 112 to reset the visual slider in its proximalmost position (thereby again exposing the indicator region 102a through the window 111), as shown in FIG. 1.

It is noted that, in alternative embodiments, one skilled in the art would readily appreciate that the present invention may be provided with only one indicator region 120a, 120b, 120c, only two indicator regions 120a, 120b, 120c (rather then three as shown in the figures), or more than three indicator regions, to indicate any combination of (a) that the clip-applying device 50 is unsqueezed, (b) that the clip applying device is in the cholangio or other mid-squeeze zone, and (c) that the clip applying device is generally fully squeezed.

The clip applying device 50 of the present invention may also include an audible and/or tactile indicating arrangement. Specifically, in the event the surgeon is too focused on the surgery at hand to look at the viewing window 111, the indicating arrangement may audibly and/or tactilely indicate to the surgeon when the clip applying device is in the cholangio zone and/or when the trigger is generally fully squeezed. Additionally, the tactile indicating arrangement of the present invention may assist the surgeon in the event that the surgeon is hearing-impaired.

As shown in FIGS. 12 and 45, an upper (first) ratchet 120 and a lower (second) ratchet 122 are affixed to and move with the trigger 64, which pivots about the trigger pivot shaft 64P. Additionally, an upper (first) pawl 124 and a lower (second) pawl 126 are pivotably affixed about a proximal paddle shaft 25P, about which the proximal paddle 25 is also affixed. Additionally, the upper pawl 124 is biased to pivot counterclockwise (when viewed in FIG. 12) by an upper spring 128, and lower pawl 126 is biased to pivot counterclockwise by a lower spring 130, the upper spring having a stronger spring force than the lower spring.

When the trigger is squeezed from the unsqueezed position toward the cholangio zone, lower spring 130 biases the lower pawl 126 to engage the lower ratchet 122 to create a ratcheting sound as the trigger is squeezed toward the cholangio zone and the upper and lower ratchets pivot counterclockwise about trigger pivot 64P (when viewed in FIG. 12), while indicator region 102a is displayed in the window 111. Once the cholangio zone is entered (and at substantially the same time the window 111 displays indicator region 102b), the upper ratchet 120 and lower ratchet 122 continue to pivot counterclockwise so that the upper ratchet engages the upper pawl 124. Specifically, when the cholangio zone is entered, the upper pawl 124 (due to the biasing force of the upper spring 128) engages the first tooth of the upper ratchet 120 to enter a first channel (cholangio channel) 120a of the upper ratchet to emit a distinct sound and transmit a distinct tactile sensation. The sound and feel of the upper pawl 124 entering the first channel 120a is significantly different than the sound and feel of ratcheting of the lower pawl 126 ratcheting with the lower ratchet 122, due to the spring force of the upper spring being greater than that of the lower spring. Additionally or alternatively, differing the dimensions and/or materials between the upper ratchet 120 and the lower ratchet 122 and/or differing the dimensions and/or materials between the upper pawl 124 and the lower pawl 126 may contribute to the differing sounds and feels when the trigger 64 is squeezed.

When the trigger 64 moves from the cholangio zone to the generally fully squeezed position (and at substantially the same time the window 111 displays indicator region 102c), the upper ratchet 120 and lower ratchet 122 continue to pivot counterclockwise such that the upper pawl moves from the cholangio channel 120a to a generally fully squeezed channel 120b, to emit the distinct sound and transmit the distinct tactile sensation. It is noted that the two distinct sounds and sensations (i.e., of the upper pawl 124 engaging the upper ratchet 120) can be made different by differing the dimensions and/or material of the cholangio channel 120a and the generally fully squeezed channel 120b. It is further noted that in alternative embodiments, the generally fully squeezed channel 120b may be eliminated, thereby alerting the surgeon only to when the clip applying device 50 is in the cholangio zone.

When the trigger 64 is released, the trigger moves to the unsqueezed position to disengage the upper pawl 124 from the upper ratchet 120, thereby resetting the clip applying device 50. The upper ratchet 120/upper pawl 124 and the lower ratchet 122/lower pawl 126 lie in different X-Y planes (different sagittal planes) so that the upper ratchet does not ever engage the lower pawl and so that the lower ratchet does not ever engage the upper pawl.

It is noted that while many of the figures show the indicating arrangement of the present invention being used in a clip applying device 50 that can accept more than one type of clip supply cartridge 68a, 68b, it should be readily understood by those skilled in the art that the indicating arrangement of present invention may be used in a clip applying device that can accept only a single type of cartridge, or alternatively, may be used in a clip applying device having clips pre-installed therein.

It is further noted that the foregoing examples have been provided merely for the purpose of explanation and are in no way to be construed as limiting of the present invention. While the present invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A trigger lockout device for a clip applying instrument, the clip applying instrument having a squeezable trigger, a barrel having a plurality of serially-installed clips therein, and a pair of jaws operatively connected to the trigger and configured to crimp a clip of the plurality of serially-installed clips, the lockout device comprising:
 a displaceable slider operatively connected to and actuable by squeezing and unsqueezing the trigger such that said slider is slidable in opposite directions along a longitudinal axial direction of the barrel;
 a block disposed within the barrel; and
 a sliding member slidable along the axial direction and having a first section having at least one aperture, and a second section, said sliding member configured such that:
 when a first number of the plurality of serially-installed clips have not been applied and when the trigger is squeezed and unsqueezed, said sliding member distally slides along the axial direction, and said slider slidably engages and displaces said block into the at least one aperture of said first section of said sliding member and slides along a path in the axial direction to retrieve a clip of the first number of the plurality of serially-installed clips, and to insert the clip into the pair of jaws; and
 when a second number of the plurality of serially-installed clips have not been applied, the second number being between and including zero and a number less than the first number, said slider engages said block such that said block abuts said second section of said sliding member and is not displaced into the at least one aperture of said first section, and such that the abutment of said block and said second section substantially prevents said slider from sliding along the path in at least one of the opposite directions such that the trigger substantially cannot be unsqueezed.

2. The lockout device according to claim 1, wherein when the second number of the plurality of serially-installed clips have not been applied, said slider engages said block to substantially prevent said slider from sliding along the path in either of the opposite directions such that the trigger substantially cannot be squeezed or unsqueezed.

3. The lockout device according to claim 1, wherein:
 the sliding member is a ladder member having a plurality of rungs comprising said first section, and having a solid surface comprising said second section, the ladder member being slidable in the axial direction to engage a rearmost clip of the plurality of serially-installed clips; wherein:
 when the first number of the plurality of serially-installed clips have not been applied, said slider displaces said block between rungs of the ladder member and out of the path;
 when the second number of the plurality of serially-installed clips have not been applied, the solid surface prevents said slider from being displaced, such that the slider engages said block to substantially prevent said slider from sliding along the path in at least one of the opposite directions such that the trigger substantially cannot be unsqueezed.

4. The lockout device according to claim 3, wherein:
 the instrument further has a spine substantially axially disposed within the barrel, the spine having an aperture configured to accept the insertion of a portion of said block therein;
 said slider is slidable along the path against an underside the spine;
 said block is connected to the underside of the spine; and
 the ladder member is slidable in the axial direction above the spine.

5. The lockout device according to claim 4, further comprising a flexible rod which connects said block to the spine.

6. The lockout device according to claim 1, wherein said slider comprises a tooth engageable with said block.

7. The lockout device according to claim 6, wherein at least one of said tooth or said slider has an angled engagement surface.

8. The lockout device according to claim 3, wherein:
 the ladder member and the plurality of serially-installed clips are disposed within a cartridge that is removable from and insertible into the barrel; and
 said slider disengages from said block when the cartridge is removed from the barrel.

9. A method for operating a clip applying instrument, the clip applying instrument having a squeezable trigger, a barrel having a block and plurality of serially-installed clips therein, a slider disposed within the barrel and operatively connected to and actuable by squeezing and unsqueezing the trigger, a sliding member having a first section having at least one aperture, and a second section, said sliding member disposed within the barrel, and a pair of jaws operatively connected to the trigger, the method comprising:
 squeezing the trigger to proximally slide the slider along a path in a generally longitudinal axial direction in relation to the barrel;
 releasing the trigger to distally slide the slider and the sliding member along the path such that the slider engages and displaces the block into the at least one aperture of the first section of the sliding member;
 inserting a clip of the plurality of clips between the pair of jaws;
 again squeezing the trigger to crimp the clip between the pair of jaws and to again proximally slide the slider along the path; and
 again releasing the trigger such that the slider engages the block such that said block abuts the second section of the sliding member and is not displaced into the at least one aperture of the first section, and such that the abutment of the block and the second section substantially prevents the slider from sliding in at least one of the proximal or distal directions and such that the trigger substantially cannot be unsqueezed.

10. The method according to claim 9, wherein said again releasing the trigger further comprises the slider engaging the block to substantially prevent the slider from sliding in the proximal and distal directions.

11. The method according to claim 9, wherein:
 the sliding member is a ladder member having a plurality of rungs at the first section, and a solid surface at the second section, the method further comprising:
 said squeezing the trigger further comprises sliding the ladder member in the axial direction and engage a rearmost clip of the plurality of serially-installed clips;
 said releasing the trigger further comprises displacing, with the slider, the block between rungs of the ladder member and out of the path; and
 said again releasing the trigger further comprises preventing, with the solid surface, the slider from being displaced, such that the slider engages the block to substantially prevent the slider from sliding along the path in at least one of the opposite directions such that the trigger substantially cannot be unsqueezed.

12. The method according to claim 11, wherein:
the instrument further has a spine substantially axially disposed within the barrel, the spine having an aperture;
the slider slides along the path against an underside the spine;
the block is connected to the underside of the spine;
the ladder member slides in the axial direction above the spine; and
said releasing the trigger further comprises displacing at least a portion of the block through the aperture.

13. The method according to claim 12, wherein the instrument further has a flexible rod which connects the block to the spine.

14. The method according to claim 9, wherein the slider has a tooth which engages the block.

15. The method according to claim 14, wherein at least one of the tooth or the slider has an angled engagement surface.

16. The method according to claim 11, wherein the ladder member and the plurality of serially-installed clips are disposed within a removable cartridge, the method further comprising:
inserting the cartridge into the barrel; and
disengaging the slider from the block when the cartridge is removed from the barrel.

17. A clip applying instrument comprising:
a squeezable trigger;
a barrel configured to accept a plurality of serially-installed clips therein,
a pair of jaws operatively connected to said trigger and configured to crimp a clip of the plurality of serially-installed clips;
a displaceable slider operatively connected to and actuable by squeezing and unsqueezing said trigger such that said slider is slidable along a path in opposite directions along a longitudinal axial direction of the barrel;
a block disposed within said barrel; and
a sliding member slidable along the axial direction and having a first section having at least one aperture, and a second section, said sliding member configured such that:
when a first number of the plurality of serially-installed clips have not been applied and when said trigger is squeezed and unsqeezed, said sliding member distally slides along the axial direction, and said slider slidably engages and displaces said block into the at least one aperture of said first section of said sliding member and slides along a path in the axial direction to retrieve a clip of the first number of the plurality of serially-installed clips, and to insert the clip into said pair of jaws; and
when a second number of the plurality of serially-installed clips have not been applied, the second number being between and including zero and a number less than the first number, said slider engages said block such that said block abuts said second section of said sliding member and is not displaced into the at least one aperture of said first section, and such that the abutment of said block and said second section substantially prevents said slider from sliding along the path in at least one of the opposite directions such that said trigger substantially cannot be unsqueezed.

18. The instrument according to claim 17, wherein said sliding member is a ladder member having a plurality of rungs comprising said first section, and having a solid surface comprising said second section, said ladder member slidable in the axial direction to engage a rearmost clip of the plurality of serially-installed clips;
wherein:
when the first number of the plurality of serially-installed clips have not been applied, said slider displaces said block between rungs of said ladder member and out of the path;
when the second number of the plurality of serially-installed clips have not been applied, said solid surface prevents said slider from being displaced, such that said slider engages said block to substantially prevent said slider from sliding along the path in at least one of the opposite directions such that said trigger substantially cannot be unsqueezed.

19. The instrument according to claim 18, further comprising a spine substantially axially disposed within said barrel, said spine having an aperture that accepts the insertion of a portion of said block therein, wherein:
said slider is slidable along the path against an underside of said spine;
said block is connected to the underside of said spine; and
said ladder member is slidable in the axial direction above said spine.

20. The instrument according to claim 18, wherein:
said ladder member and the plurality of serially-installed clips are disposed within a cartridge that is removable from and insertible into said barrel; and
said slider disengages from said block when the cartridge is removed from said barrel.

* * * * *